United States Patent
Schuman, Sr. et al.

(10) Patent No.: US 8,384,526 B2
(45) Date of Patent: Feb. 26, 2013

(54) INDICATOR APPARATUS FOR HEALTHCARE COMMUNICATION SYSTEM

(75) Inventors: Richard J. Schuman, Sr., Cary, NC (US); Williams F. Collins, Jr., Columbus, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 965 days.

(21) Appl. No.: 12/369,779

(22) Filed: Feb. 12, 2009

(65) Prior Publication Data

US 2009/0214009 A1  Aug. 27, 2009

Related U.S. Application Data

(60) Provisional application No. 61/066,883, filed on Feb. 22, 2008, provisional application No. 61/066,877, filed on Feb. 22, 2008, provisional application No. 61/066,882, filed on Feb. 22, 2008, provisional application No. 61/066,918, filed on Feb. 22, 2008, provisional application No. 61/145,306, filed on Jan. 16, 2009.

(51) Int. Cl.
  *G08B 5/22* (2006.01)
(52) U.S. Cl. ........... 340/286.07; 340/573.1; 340/286.06; 340/332; 379/106.2
(58) Field of Classification Search ............ 340/815.4, 340/815.45, 286.06, 286.07, 573.1, 332, 340/691.4; 362/215, 225, 236; 379/106.02
See application file for complete search history.

(56) References Cited

U.S. PATENT DOCUMENTS

| | | |
|---|---|---|
| 2,330,356 A | 9/1943 | Belliveau |
| 2,335,524 A | 11/1943 | Lomax |
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |

(Continued)

FOREIGN PATENT DOCUMENTS

| | | |
|---|---|---|
| EP | 1 623 666 A2 | 2/2006 |
| EP | 1 679 648 A1 | 7/2006 |

(Continued)

OTHER PUBLICATIONS

European Search Report for EP 09 25 0419, dated Aug. 13, 2010, (7 pages).

(Continued)

*Primary Examiner* — Anh V La
(74) *Attorney, Agent, or Firm* — Barnes & Thornburg LLP

(57) ABSTRACT

An indicator apparatus is configurable for use in a healthcare communication system, such as a nurse call system. The indicator apparatus includes a visual indicator. The visual indicator is operable to selectively display one or more colors in response to calls received by the healthcare communication system.

18 Claims, 20 Drawing Sheets

U.S. PATENT DOCUMENTS

| | | |
|---|---|---|
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Chahariiran |
| 4,907,845 A | 3/1990 | Wood |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser |
| 5,075,523 A | 12/1991 | Ford |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,140,309 A | 8/1992 | Gusakov |
| 5,153,584 A | 10/1992 | Engira |
| 5,235,258 A | 8/1993 | Schuerch |
| 5,266,944 A | 11/1993 | Carroll et al. |
| 5,276,680 A | 1/1994 | Messenger |
| 5,291,399 A | 3/1994 | Chaco |
| 5,319,355 A | 6/1994 | Russek |
| 5,319,363 A | 6/1994 | Welch et al. |
| 5,327,592 A | 7/1994 | Stump |
| 5,351,439 A | 10/1994 | Takeda et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,430,900 A | 7/1995 | Kim |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,511,256 A | 4/1996 | Capaldi |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,564,108 A | 10/1996 | Hunsaker et al. |
| 5,568,119 A | 10/1996 | Schipper et al. |
| 5,576,452 A | 11/1996 | Dever et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,600,214 A | 2/1997 | Fromson |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,649,833 A | 7/1997 | Pfeuffer et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,714,548 A | 2/1998 | Ma et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,781,921 A | 7/1998 | Nichols |
| 5,787,528 A | 8/1998 | Antinori |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,901,391 A | 5/1999 | Kato |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,956,539 A | 9/1999 | Fitterman et al. |
| 5,963,126 A * | 10/1999 | Karlin et al. .................. 340/321 |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,346 A * | 1/2000 | Malone ........................... 368/10 |
| 6,014,633 A | 1/2000 | DeBusk et al. |
| 6,037,723 A | 3/2000 | Shafer et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,078,261 A | 6/2000 | Davsko |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,101,644 A | 8/2000 | Gagneur et al. |
| 6,111,509 A | 8/2000 | Holmes |
| 6,125,350 A | 9/2000 | Dirbas |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,241,668 B1 | 6/2001 | Herzog |
| 6,249,221 B1 * | 6/2001 | Reed ........................ 340/539.14 |
| 6,259,355 B1 | 7/2001 | Chaco et al. |
| 6,264,614 B1 | 7/2001 | Albert et al. |
| 6,272,347 B1 | 8/2001 | Griffith et al. |
| 6,279,183 B1 | 8/2001 | Kummer et al. |

| | | | | | | |
|---|---|---|---|---|---|---|
| 6,287,253 B1 | 9/2001 | Ortega et al. | | 6,731,989 B2 | 5/2004 | Engleson et al. |
| 6,302,844 B1 | 10/2001 | Walker et al. | | 6,740,033 B1 | 5/2004 | Olejniczak et al. |
| 6,314,556 B1 | 11/2001 | DeBusk et al. | | 6,749,566 B2 | 6/2004 | Russ |
| 6,320,510 B2 | 11/2001 | Menkedick et al. | | 6,751,630 B1 | 6/2004 | Franks et al. |
| 6,340,868 B1 * | 1/2002 | Lys et al. .......... 315/185 S | | 6,754,545 B2 | 6/2004 | Haeuser et al. |
| 6,344,794 B1 | 2/2002 | Ulrich et al. | | 6,754,883 B2 | 6/2004 | DeBusk et al. |
| 6,348,777 B1 | 2/2002 | Brown et al. | | 6,759,607 B2 | 7/2004 | Engler |
| 6,362,725 B1 | 3/2002 | Ulrich et al. | | 6,759,959 B2 | 7/2004 | Wildman |
| 6,364,834 B1 | 4/2002 | Reuss et al. | | 6,763,541 B2 | 7/2004 | Mahoney et al. |
| 6,398,727 B1 | 6/2002 | Bui et al. | | 6,771,172 B1 | 8/2004 | Robinson et al. |
| 6,406,426 B1 | 6/2002 | Reuss et al. | | 6,773,396 B2 | 8/2004 | Flach et al. |
| 6,407,335 B1 | 6/2002 | Franklin-Lees et al. | | 6,778,225 B2 | 8/2004 | David |
| 6,412,980 B1 | 7/2002 | Lounsberry et al. | | 6,781,517 B2 | 8/2004 | Moster et al. |
| 6,416,471 B1 | 7/2002 | Kumar et al. | | 6,784,797 B2 | 8/2004 | Smith et al. |
| 6,421,649 B1 | 7/2002 | Rattner | | 6,788,206 B1 | 9/2004 | Edwards |
| 6,439,769 B1 | 8/2002 | Polkus et al. | | 6,791,460 B2 | 9/2004 | Dixon et al. |
| 6,441,742 B1 | 8/2002 | Lovely et al. | | 6,792,396 B2 | 9/2004 | Inda et al. |
| 6,442,290 B1 | 8/2002 | Ellis et al. | | 6,801,227 B2 | 10/2004 | Bocionek et al. |
| 6,445,299 B1 | 9/2002 | Rojas, Jr. | | 6,807,543 B2 | 10/2004 | Muthya |
| 6,450,956 B1 | 9/2002 | Rappaport et al. | | 6,825,763 B2 | 11/2004 | Ulrich et al. |
| 6,462,656 B2 | 10/2002 | Ulrich et al. | | 6,826,578 B1 | 11/2004 | Brackett et al. |
| 6,483,264 B1 | 11/2002 | Shafer et al. | | 6,828,992 B1 | 12/2004 | Freeman et al. |
| 6,486,792 B1 | 11/2002 | Moster et al. | | 6,829,796 B2 | 12/2004 | Salvatini et al. |
| 6,493,568 B1 | 12/2002 | Bell et al. | | 6,830,549 B2 | 12/2004 | Bui et al. |
| 6,494,831 B1 | 12/2002 | Koritzinsky | | 6,832,199 B1 | 12/2004 | Kucek et al. |
| 6,510,344 B1 | 1/2003 | Halpern | | 6,840,117 B2 | 1/2005 | Hubbard, Jr. |
| 6,516,324 B1 | 2/2003 | Jones et al. | | 6,847,814 B1 | 1/2005 | Vogeleisen |
| 6,526,310 B1 | 2/2003 | Carter et al. | | 6,864,795 B2 | 3/2005 | Smith et al. |
| 6,529,164 B1 | 3/2003 | Carter | | 6,868,256 B2 | 3/2005 | Dooley et al. |
| 6,533,453 B1 | 3/2003 | Heidsieck et al. | | 6,870,484 B1 | 3/2005 | Brinsfield et al. |
| 6,535,576 B2 | 3/2003 | Vafi et al. | | 6,871,211 B2 | 3/2005 | Labounty et al. |
| 6,539,393 B1 | 3/2003 | Kabala | | 6,873,884 B2 | 3/2005 | Brackett et al. |
| 6,544,173 B2 | 4/2003 | West et al. | | 6,876,303 B2 | 4/2005 | Reeder et al. |
| 6,544,174 B2 | 4/2003 | West et al. | | 6,876,985 B2 | 4/2005 | Kawanaka |
| 6,551,243 B2 | 4/2003 | Bocionek et al. | | 6,885,288 B2 | 4/2005 | Pincus |
| 6,553,105 B2 | 4/2003 | Chea, Jr. et al. | | 6,891,909 B2 | 5/2005 | Hurley et al. |
| 6,553,106 B1 | 4/2003 | Gould et al. | | 6,892,083 B2 | 5/2005 | Shostak |
| 6,554,174 B1 | 4/2003 | Aceves | | 6,904,161 B1 | 6/2005 | Becker et al. |
| 6,556,630 B1 | 4/2003 | Brinsfield et al. | | 6,909,995 B2 | 6/2005 | Shiraishi |
| 6,560,224 B1 | 5/2003 | Kung et al. | | 6,912,549 B2 | 6/2005 | Rotter et al. |
| 6,560,274 B1 | 5/2003 | Leitgeb et al. | | 6,915,170 B2 | 7/2005 | Engleson et al. |
| 6,572,556 B2 | 6/2003 | Stoycos et al. | | 6,925,367 B2 | 8/2005 | Fontius |
| 6,575,901 B2 | 6/2003 | Stoycos et al. | | 6,930,878 B2 | 8/2005 | Brackett et al. |
| 6,581,204 B2 | 6/2003 | DeBusk et al. | | 6,958,706 B2 | 10/2005 | Chaco et al. |
| 6,584,182 B2 | 6/2003 | Brodnick | | 6,968,375 B1 | 11/2005 | Brown |
| 6,584,454 B1 | 6/2003 | Hummel, Jr. et al. | | 6,982,639 B2 | 1/2006 | Brackett et al. |
| 6,585,645 B2 | 7/2003 | Hutchinson | | 6,988,989 B2 | 1/2006 | Weiner et al. |
| 6,589,170 B1 | 7/2003 | Flach et al. | | 6,998,986 B2 | 2/2006 | Smith |
| 6,593,528 B2 | 7/2003 | Franklin-Lees et al. | | 7,020,921 B2 | 4/2006 | Wang |
| 6,594,146 B2 | 7/2003 | Frangesch et al. | | 7,023,821 B2 | 4/2006 | Wotherspoon et al. |
| 6,594,519 B2 | 7/2003 | Stoycos et al. | | 7,038,584 B2 | 5/2006 | Carter |
| 6,600,421 B2 | 7/2003 | Freeman | | 7,053,767 B2 | 5/2006 | Petite et al. |
| 6,603,494 B1 | 8/2003 | Banks et al. | | 7,061,396 B1 | 6/2006 | Conrad et al. |
| 6,609,115 B1 | 8/2003 | Mehring et al. | | 7,068,143 B2 | 6/2006 | Doering et al. |
| 6,616,606 B1 | 9/2003 | Petersen et al. | | 7,071,820 B2 | 7/2006 | Callaway |
| 6,622,088 B2 | 9/2003 | Hood | | 7,079,036 B2 | 7/2006 | Cooper et al. |
| 6,640,246 B1 | 10/2003 | Gary, Jr. et al. | | 7,088,235 B1 | 8/2006 | Carricut |
| 6,643,238 B2 | 11/2003 | Nakajima | | 7,092,376 B2 | 8/2006 | Schuman |
| 6,650,346 B1 | 11/2003 | Jaeger et al. | | 7,107,642 B2 | 9/2006 | Wong et al. |
| 6,659,947 B1 | 12/2003 | Carter et al. | | 7,138,902 B2 | 11/2006 | Menard |
| 6,665,358 B1 | 12/2003 | Oldagiri | | 7,151,457 B2 | 12/2006 | Riley et al. |
| 6,665,385 B2 | 12/2003 | Rogers et al. | | 7,160,133 B2 | 1/2007 | Karadimas et al. |
| 6,665,820 B1 | 12/2003 | Frowein et al. | | 7,248,881 B2 | 7/2007 | Shostak |
| 6,669,630 B1 | 12/2003 | Joliat et al. | | 7,263,669 B2 | 8/2007 | Denholm |
| 6,671,547 B2 | 12/2003 | Lyster et al. | | 7,275,220 B2 | 9/2007 | Brummel et al. |
| 6,671,563 B1 | 12/2003 | Engelson et al. | | 7,290,299 B2 | 11/2007 | Votel |
| 6,685,633 B2 | 2/2004 | Albert et al. | | 7,292,135 B2 | 11/2007 | Bixler et al. |
| 6,689,091 B2 | 2/2004 | Bui et al. | | 7,299,512 B2 | 11/2007 | Cavalier et al. |
| 6,693,513 B2 | 2/2004 | Tuttle | | 7,301,451 B2 | 11/2007 | Hastings |
| 6,693,514 B2 | 2/2004 | Perea, Jr. et al. | | 7,307,522 B2 | 12/2007 | Dawson |
| 6,694,367 B1 | 2/2004 | Miesbauer et al. | | 7,310,541 B2 | 12/2007 | Shostak |
| 6,694,509 B1 | 2/2004 | Stoval et al. | | 7,319,386 B2 | 1/2008 | Collins, Jr. et al. |
| 6,697,765 B2 | 2/2004 | Kuth | | 7,333,002 B2 | 2/2008 | Bixler et al. |
| 6,707,476 B1 | 3/2004 | Hochstedler | | 7,336,187 B2 | 2/2008 | Hubbard, Jr. et al. |
| 6,714,913 B2 | 3/2004 | Brandt et al. | | 2001/0050610 A1 | 12/2001 | Gelston |
| 6,721,818 B1 | 4/2004 | Nakamura | | 2001/0051765 A1 | 12/2001 | Walker et al. |
| 6,726,634 B2 | 4/2004 | Freeman | | 2002/0014951 A1 | 2/2002 | Kramer et al. |
| 6,727,818 B1 | 4/2004 | Wildman et al. | | 2002/0032583 A1 | 3/2002 | Joao |
| 6,731,311 B2 | 5/2004 | Bufe et al. | | 2002/0044043 A1 | 4/2002 | Chaco et al. |

| | | |
|---|---|---|
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0101349 A1 | 8/2002 | Rojas, Jr. |
| 2002/0103674 A1 | 8/2002 | Reeder et al. |
| 2002/0151990 A1 | 10/2002 | Ulrich et al. |
| 2002/0173991 A1 | 11/2002 | Avitall |
| 2002/0186136 A1 | 12/2002 | Schuman |
| 2002/0196141 A1 | 12/2002 | Boone et al. |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0179099 A1 | 9/2003 | Perea, Jr. et al. |
| 2003/0197614 A1 | 10/2003 | Smith et al. |
| 2003/0206116 A1 | 11/2003 | Weiner et al. |
| 2003/0212575 A1 | 11/2003 | Saalsaa et al. |
| 2003/0230469 A1 | 12/2003 | Engler |
| 2004/0064890 A1 | 4/2004 | Kim et al. |
| 2004/0158922 A1 | 8/2004 | Eberler et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2004/0222897 A1 | 11/2004 | Schuhmann et al. |
| 2004/0243446 A1 | 12/2004 | Wyatt |
| 2004/0249670 A1 | 12/2004 | Noguchi et al. |
| 2004/0261184 A1 | 12/2004 | Flick |
| 2005/0035862 A1 | 2/2005 | Wildman et al. |
| 2005/0055779 A1 | 3/2005 | Damewood |
| 2005/0076441 A1 | 4/2005 | Dominati et al. |
| 2005/0110617 A1 | 5/2005 | Kile et al. |
| 2005/0155149 A1 | 7/2005 | Pedersen |
| 2005/0168341 A1 | 8/2005 | Reeder et al. |
| 2005/0170863 A1 | 8/2005 | Shostak |
| 2005/0206505 A1 | 9/2005 | Arcaria |
| 2005/0242946 A1 | 11/2005 | Hubbard, Jr. et al. |
| 2006/0046579 A1 | 3/2006 | Karadimas et al. |
| 2006/0049936 A1 | 3/2006 | Collins, Jr. et al. |
| 2006/0114854 A1 | 6/2006 | Wotherspoon et al. |
| 2006/0126560 A1 | 6/2006 | Wotherspoon et al. |
| 2006/0136265 A1 | 6/2006 | Summers et al. |
| 2006/0214786 A1 | 9/2006 | Bixler et al. |
| 2006/0220798 A1 | 10/2006 | Willis |
| 2006/0239195 A1 | 10/2006 | Camins et al. |
| 2006/0248221 A1 | 11/2006 | Hottel et al. |
| 2006/0267740 A1 | 11/2006 | Bixler et al. |
| 2007/0071114 A1 | 3/2007 | Sanderford, Jr. et al. |
| 2007/0135688 A1 | 6/2007 | Brown |
| 2007/0156456 A1 | 7/2007 | McGillin et al. |
| 2007/0210917 A1 | 9/2007 | Collins, Jr. et al. |
| 2007/0229249 A1 | 10/2007 | McNeal et al. |
| 2007/0237487 A1 | 10/2007 | Lin |
| 2007/0239484 A1 | 10/2007 | Around et al. |
| 2007/0257788 A1 | 11/2007 | Carlson et al. |
| 2008/0004904 A1 | 1/2008 | Tran |
| 2008/0015900 A1 | 1/2008 | Denholm |
| 2008/0018436 A1 | 1/2008 | Traughber et al. |
| 2008/0027754 A1 | 1/2008 | Auker et al. |

FOREIGN PATENT DOCUMENTS

| | | |
|---|---|---|
| GB | 250 769 | 4/1926 |
| JP | 1-76197 | 3/1989 |
| WO | 9523378 A2 | 8/1995 |
| WO | 9808203 A1 | 2/1998 |
| WO | WO 02/091297 | 11/2002 |
| WO | WO 2004/036390 | 4/2004 |

OTHER PUBLICATIONS

Hill-Rom A Hillenbrand Industry, The COMposer® System Installation Manual, 2003.
Hill-Rom A Hillenbrand Industry, The COMposer Communication System Service Manual, 1995.
Hill-Rom a Hillenbrand Industry, COMLinx™ Enterprise Solutions Nurse Communication Module, User's Guide, 2000.
GE Telligence™ System Overview (5 pages).
Partial European Search report from EP 09 25 0420 date Jun. 16, 2009.
(Online) XP002530934 Hill-Rom Technical Brief, www.hill-rom/canada/PDF/144097.pdf, "CONLinx Nurse Communication Module Technological Advances", Jul. 13, 2006, 4 pages.
European Search Report for Application No./Patent No. 12164817.4-2215/2495708, dated Sep. 3, 2012, 9 pages.
European Search Report for Application No./Patent No. 12164815.8-2215/2495712, dated Sep. 3, 2012, 8 pages.
European Search Report for Application No./Patent No. 12164812.5-2215/2495711, dated Sep. 3, 2012, 8 pages.
"COMLinx Nurse Communication Module Technological Advances," Internet Citation, Jan. 1, 2006, retrieved from http://www.hillrom.com/canada/PDF/144097.pdf on Jun. 16, 2009, 4 pages.

* cited by examiner

INDICATOR APPARATUS FOR HEALTHCARE COMMUNICATION SYSTEM

RELATED APPLICATIONS

This application claims the benefit of U.S. Provisional Patent Application Ser. No. 61/066,883, filed Feb. 22, 2008, and claims the benefit of U.S. Provisional Patent Application Ser. No. 61/066,877 filed Feb. 22, 2008, and claims the benefit of U.S. Provisional Patent Application Ser. No. 61/066,882 filed Feb. 22, 2008, and claims the benefit of U.S. Provisional Patent Application Ser. No. 61/066,918, filed Feb. 22, 2008, and claims the benefit of U.S. Provisional Patent Application Ser. No. 61/145,306, filed Jan. 16, 2009, all of which are incorporated herein by this reference.

BACKGROUND

The present disclosure relates generally to healthcare communication systems such as patient-nurse communication systems, and more particularly to indicator assemblies usable in connection with such systems.

Healthcare communication systems such as patient-nurse communication systems or "nurse call" systems enable communication among members of a nursing staff and other persons dispersed throughout a healthcare facility. Such systems generally provide information about the current status or condition of patients in the facility, and enable voice communication between patients and staff members through a telecommunications infrastructure.

Visual indicators are often positioned at various locations throughout a facility to visually notify staff when events or conditions relating to patients located in various parts of a healthcare facility occur, so that they can be attended to in a timely manner. One example of a known nurse call system that includes an indicator assembly is Hill-Rom's COMLINX® system. Another example of an existing indicator assembly or "dome light" is the Infinity™ dome light provided in connection with the Telligence™ system offered by GE Security.

There is still a need for advanced healthcare communication system capabilities directed to improving nursing staff and overall hospital efficiency. Additional or improved features that are directed to reducing the risk of adverse patient conditions occurring in the facility are also needed. However, as cost is often a concern to these facilities, advancements that can be achieved while containing or reducing the costs of implementing, maintaining and operating these systems are desired.

SUMMARY

This disclosure describes an indicator assembly for a patient-nurse communication system.

One embodiment of an indicator apparatus for a patient-nurse communication system includes a base mountable to a wall or a ceiling, and at least one visual indicator supported by the base. The at least one visual indicator is configured to display one or more of a plurality of colors. The apparatus also includes electrical circuitry operably coupled to the at least one visual indicator. The electrical circuitry is configured to receive electrical signals indicative of at least one color to be displayed by the at least one visual indicator in response to a call from a call-originating device of a patient-nurse communication system. The at least one color to be displayed is variable depending on a call type.

The indicator apparatus may include a plurality of visual indicators. The visual indicators are operably coupled to the electrical circuitry to display at least one color in response to calls from a call-originating device of a patient-nurse communication system. The electrical circuitry may be configured to send a first electrical signal indicative of at least one color to a first visual indicator of the plurality of visual indicators in response to a first call. The electrical circuitry may be configured to send a second electrical signal indicative of at least one color to a second visual indicator of the plurality of visual indicators in response to a second call.

The indicator apparatus may include a speaker, wherein the electrical circuitry is configured to receive an electrical signal from the patient-nurse communication system to play a sound file through the speaker in response to a call from a call-originating device of the patient-nurse communication system. The sound file to be played may be variable depending on a call type.

The indicator apparatus may include one or more visual indicators, each of which has a length, a width, and a thickness. The thickness of the visual indicator may be less than the length. The thickness of the visual indicator may also be less than the width.

The indicator apparatus may include a cover, which defines an interior region. One or more of the visual indicators may be positioned in the interior region. The cover may have first and second faces that are spaced by a thickness. The first and second faces of the cover may be substantially parallel.

The color to be displayed by the visual indicator or indicators may be variable depending on criteria relating to a call-originating device, a call type, a call priority, and/or a patient location.

In another embodiment, a patient-nurse communication system includes an indicator apparatus. The indicator apparatus includes a base mountable to a wall or a ceiling, a multi-color light source supported by the base, and electrical circuitry operably coupled to the light source. The electrical circuitry is configured to receive electrical signals from the patient-nurse communication system indicative of at least one color to be displayed by the light source. The system also includes a memory comprising at least one parameter relating to a call from a call-originating device of the patient-nurse communication system. The system also includes computer circuitry configured to access the memory, read the at least one parameter, identify at least one color to be illuminated by the light source based on the at least one parameter, and send an electrical signal to the light source to illuminate the at least one selected color in response to the call. One or more of the parameters may associate a call type of a call from a call-originating device with a color.

The indicator assembly may include a speaker. The computer circuitry may be configured to execute computer program logic to select a sound file in response to a call from a call-originating device of the patient-nurse communication system and send an electrical signal to the indicator assembly to play the sound file through the speaker in response to the call.

The system may include a memory, wherein the sound file is one of a plurality of sound files stored in the memory. The computer circuitry may be configured to receive data indicative of changes to the at least one parameter from a network and store the parameter changes in the memory.

The system may include a visual indicator illuminatable by the light source. The visual indicator may have a length, a width, and a thickness, and the thickness of the visual indicator may be less than the length. The thickness of the visual indicator may be less than the width.

The system may include a visual indicator that has a first face and a second face spaced from the first face by the thickness to define an interior region of the visual indicator, and the interior region of the visual indicator comprises plastic.

The indicator assembly may include a cover defining an interior region. One or more visual indicators may be positioned in the interior region. The visual indicator(s) may be illuminatable by the light source. The cover may have first and second faces that are spaced by a thickness. The first and second faces may be substantially parallel.

The visual indicator may include a plurality of light guides positioned in the interior region. The light guides may be aligned in a plane that is substantially parallel to the first and second faces of the cover.

In another embodiment, an indicator apparatus for a patient-nurse communication system includes an indicator housing, a cover coupled to the indicator housing and defining an interior region, and a plurality of visual indicators extending from the indicator housing and located in the interior region of the cover. The visual indicators are selectively illuminatable in response to signals received from a call-originating device of a patient-nurse communication system. The apparatus also includes a mounting plate coupled to the indicator housing. The mounting plate includes a first mounting portion and a second mounting portion spaced from the first mounting portion. Each mounting portion has a plurality of vertically aligned and laterally elongated mounting ports.

The indicator housing may have a first thickness. The apparatus may further include a second housing spaced from the indicator housing and defining a second interior region. Electronic circuitry may be located in the second interior region. The electronic circuitry may be operably coupled to the visual indicators. The second housing may have a second thickness, wherein the first thickness is less than the second thickness.

The indicator housing may be mountable to the first mounting portion and the second housing may be mountable to the second mounting portion.

The indicator assembly may include an elongated slot defined by the indicator housing, wherein the slot is configured to receive a visual indicator in either a first orientation or a second orientation substantially perpendicular to the first orientation.

Patentable subject matter may include one or more features or combinations of features shown or described anywhere in this disclosure including the written description, drawings, and claims.

BRIEF DESCRIPTION OF THE DRAWINGS

The detailed description refers to the following figures in which.

DETAILED DESCRIPTION

Aspects of the present invention are described with reference to certain illustrative embodiments shown in the accompanying drawings and described herein.

In general, a healthcare communication system includes one or more staff or nursing computers or computing devices, which may be referred to as stations or consoles. The stations or consoles, in cooperation with various computers, networks, and supporting equipment and services, enable nurses and other staff to receive, view, manage, and route, output or respond to electrical and wireless signals from a variety of communication, call, monitoring, detecting and/or signaling devices. Some communication, call, monitoring, detecting and/or signaling devices are operated by patients, staff, or visitors. Others are activated by the occurrence of an event or condition detected by signal receivers, patient monitoring equipment or hospital beds located throughout a healthcare facility. When the system receives a signal from a communication, call, monitoring, detecting and/or signaling device, one or more indicator assemblies may be activated to alert hospital staff of the condition or event being signaled by the communication, call, monitoring, detecting and/or signaling device.

Figure 1:
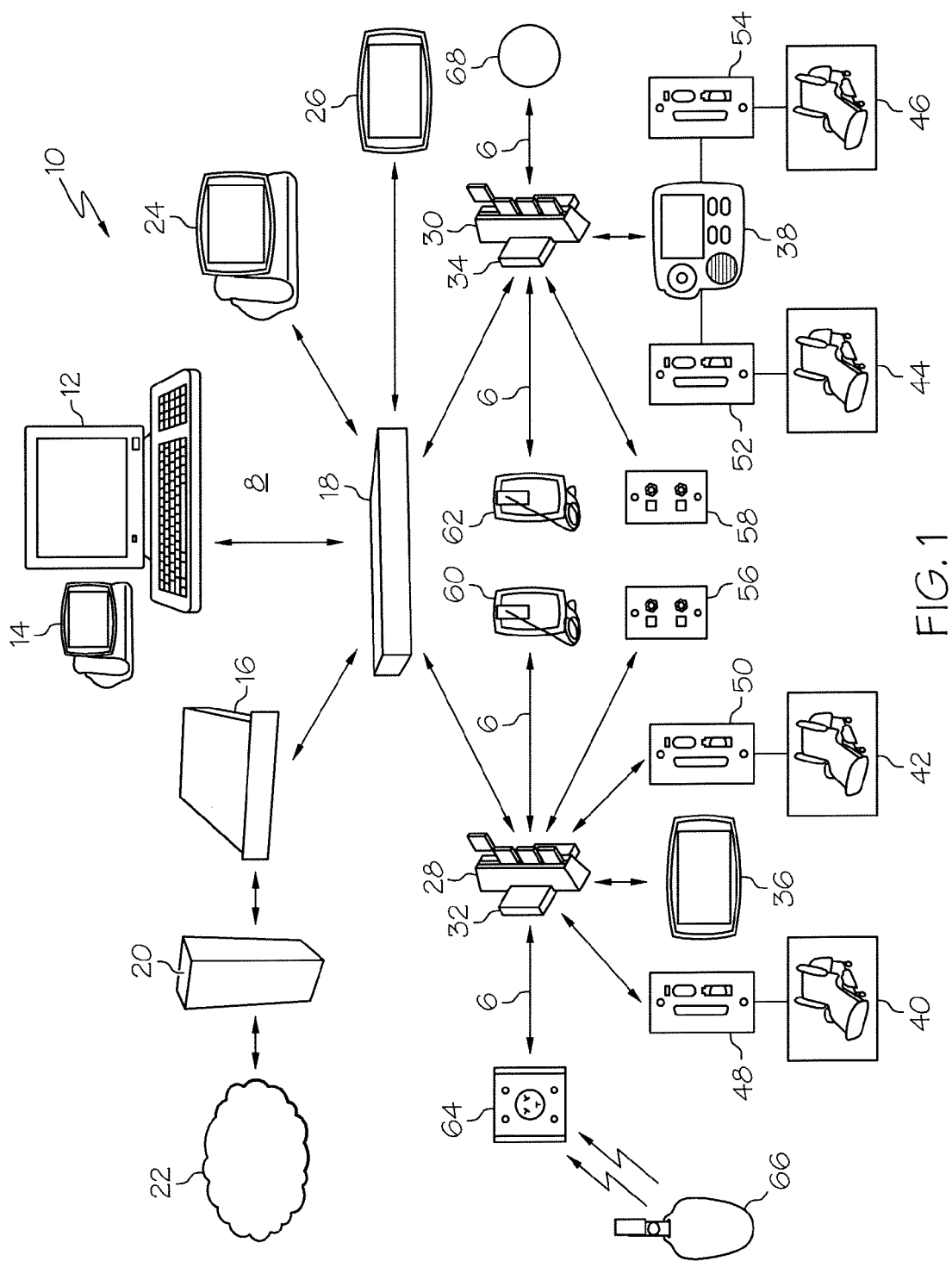
FIG. 1 is a simplified schematic showing a logical architecture for a patient-nurse communication system including at least one indicator assembly in communication with other components of the system.

One embodiment of a patient-nurse communication system 10 is diagrammatically illustrated in FIG. 1. System 10 includes a primary console 12, and one or more secondary consoles 14, 24, 26, 36, 38 which are configured to be operated by nurses or other staff. Primary console 12 enables nurses or staff to monitor activity and communicate with patients and other staff within the facility or portion of the facility monitored by the system. Primary console 12 is a computer or computing device that has a display screen, voice communication capabilities, and one or more input devices (such as a keyboard, touch screen, mouse, switch, button, knob, or the like) configured to control the operation of the patient-nurse communication system. Voice communication capabilities are provided by an integrated microphone and speaker and/or a telephone handset.

Primary console or station 12,14 is configured to enable a nurse or other staff to place calls, cancel calls, monitor the location of other staff members, process calls and alerts and route or relay calls or alerts to and from other consoles or other components of the system. Primary console 12 may further be configured to enable an authorized user to update the status of calls, alerts, monitored persons and/or monitored devices or equipment, and enable or disable calls or alerts. Primary station 14 is configured to be desk-mounted but could also be wall-mounted.

Secondary consoles or stations 24, 26, 36, 38 have similar components and provide similar but often more limited capabilities than the primary console 12, 14. For example, primary console 12 may include a larger display screen, a graphical user interface configured for data entry, monitoring, and analysis, a network interface (e.g., for TCP/IP connectivity), and/or a telephone handset. However, different configurations of secondary consoles 24, 26, 36, 38 exist that may or may not have a graphical display or telephone handset, or may have limited network connectivity.

For example, console 24 has structural components that are similar to console 14 but generally does not have all the same functional capabilities as console 14 because console 24 is a secondary console. Console 24 may be configured to display only a subset of the information that is available at console 14 (i.e., console 24 may be configured to display only calls pertaining to a particular grouping of patient rooms assigned to a specific nurse, while console 14 is configured to display all call information for all rooms in a nursing unit, group of units or entire facility). Consoles 26, 36 have similar structural components and functional capabilities as console 24 but do not have a telephone handset. Console 38 is a scaled-down and potentially lower cost version of console 24, and as such has more limited graphic capabilities and restricted network connectivity.

Notwithstanding the above description, secondary consoles 24, 26, 36, 38 may have all of the components and functional capabilities as primary console. For example, a console or station may be a primary console for one nursing unit, zone or portion of a facility and also be configured as a secondary console for another unit, zone or portion of the facility. In this way, information for multiple units, zones or portions of a facility may be monitored from one station or console.

Consoles 12, 14, 24, 36, 38 are connected either directly or indirectly (i.e., through an input-output board) to a switch 18. In the illustrated embodiment, switch 18 is a Power over Ethernet (POE) switch, however, other suitable types of switches may be used, as will be understood by those skilled in the art. Switch 18 and electronic assemblies or input-output boards 32, 34 provide connectivity to a variety of call, communication, monitoring, detecting and/or signaling devices 40, 42, 44, 46, 48, 50, 52, 54, 56, 58, 60, 62, 64, 66, 68 to receive call and/or alert signals therefrom. Switch 18 may also be configured to provide electrical power to remote devices, as is the case with POE switches.

In general, "console" or "station" is used herein to refer to a computer or computing device configured to provide an interface to the system for a user, such as a nurse, staff member, patient, or visitor. As such, these equipment include at least one output device, such as a visual display or speaker, to notify or communicate calls and/or other information to the user. Stations or consoles may also include at least one input device, such as a touchscreen, keypad or keyboard, microphone, telephone handset, push button, switch, dial, lever, or the like, to enable the user to place and/or respond to the calls or other information. Stations or consoles also include circuitry to connect them to the system 10. Stations or consoles include embodiments that may be desk- or table-mounted, as well as embodiments that may be mounted to a wall, head-wall, column, bed, siderail, or other structure.

Input/output boards 32, 34 are circuit board assemblies that provide computing processing and wiring for a patient location in the healthcare facility, such as a patient room. Among other things, the I/O boards operate to convert device-specific protocols from a variety of devices, which may be installed in patient rooms, to a single network protocol suitable for communication over a network. For example, I/O boards 32, 34 convert serial links to primary and secondary consoles, remote locating receiver or bed interface unit room bus protocols, and serial to dome light protocols, on the one side, to XML-over-TCP/IP on the other side. In the illustrated embodiments, each I/O board 32, 34 includes a multimedia microprocessor with built-in multimedia capability, such as the Freescale IMX 27. Input-output boards 32, 34 may also include one or more POE ports to enable devices to connect directly to the board instead of connecting to the system through a switch.

Indicator assemblies 28, 30 are coupled to input-output boards 32, 34 and receive control signals therefrom to activate a visual or audible notification, or a combination of visual and audible notifications, at the indicator assembly. There are many different terms that refer to devices that have capabilities of indicator assemblies, including "dome light," "zone light," "corridor lamp," "signaling device," "indicator," and "annunciator." For ease of description, this disclosure may refer to such devices individually or collectively as an "indicator assembly" or "indicator" in the singular or plural form.

In general, primary console 12 is in communication with input-output boards 32, 34 through a computer network 8 and switch 18. Secondary consoles 14, 24, 26, 36, 38 are in communication with primary console 12 over network 8 through a switch 18 and may thereby receive information and commands from primary console 12. In the illustrated embodiment, network 8 is a TCP/IP network running an XML data protocol configured to enable communication among a number of devices and/or systems usable by the healthcare facility.

Call, communication, monitoring, detecting and/or signaling devices include, for example: beds 40, 42, 44, 46 (such as Hill-Rom TotalCare® or VersaCare® beds), which are linked to system 10 via bed interface units 48, 50, audio bed station connectors (ASBCs) 52, 54, or similar bed connector devices; patient monitors and other medical or clinical devices or equipment (such as therapy equipment, heart rate or respiration monitoring devices, and the like), which are linked to system 10 via connectors 56, 58; call cords 60, 62; wireless (i.e. infrared or radio frequency) location tracking receivers or "remote location receivers" 64 and related location tracking badges or tags 66, and smoke alarm 68. Some call, communication, monitoring, detecting and/or signaling devices, such as remote receiver 64, cords 60, 62, smoke alarm 68 and bed interface units 48, 50, are coupled directly to I/O boards 32, 34 by communication links 6. Other devices are coupled to I/O boards 32, 34 indirectly through consoles or stations, such as ASBCs 52, 54, which connect beds 44, 46 to station 38. In the illustrated embodiment, links 6 are RS485 connections.

For ease of description, this disclosure may use "incoming call" or "call" to refer to one or more calls, messages, communications or signals sent from a call, communication, detecting, monitoring, and/or signaling device to system 10, and may use "outgoing notification", or "notification" to refer to one or more calls, messages, communications, alarm signals, alert signals or other indications or annunciations that are configured to notify or otherwise direct the attention of a nurse or other staff member of or associated with the facility to an incoming call. Further, this disclosure may use "call device" to refer individually or collectively to such call, communication, detecting, monitoring, and/or signaling devices.

As shown in FIG. 1, switch 18 links various components of system 10 to a primary station 12, 14. Primary station 12, 14, alone or in combination with one or more other server computers and/or computing devices, hosts and executes software and services needed to operate system 10. Primary station computer 14 is configured to process control messages generated by system 10 and send them to the appropriate destination or endpoint, such as a secondary console or I/O board. As such, server 14 includes a soft telephony switch and related componentry.

Server 14 is configured to operate and manage many of the primary nurse call functions of system 10, such as receiving and managing messages from various connected devices, synchronizing devices that come online, controlling placement and canceling of calls, answering of calls, generating of notifications or alerts, acknowledging and canceling of notifications and alerts, managing location information for staff and devices, activating and deactivating staff, managing staff-patient assignments, assigning and managing roles and responsibilities to staff and devices, and managing patient information and patient discharges and transfers.

Switch 18 may also link system 10 to an "enterprise" server 16. Enterprise server 16 may be configured to enable system 10 to interface with systems or services that are considered "external" or "optional" to system 10. For example, server 16 may be coupled to a telecommunications server 20, which acts as a gateway to a facility's telecommunications infrastructure 22. Infrastructure 22 generally includes a network that is configured to facilitate communication among a variety of telecommunication devices, including analog and digital devices, fixed telephones and mobile or cellular devices, personal data assistants (PDAs), pagers and the like. For example, infrastructure 22 may include a public switched telephone network (PSTN) or private branch exchange (PBX) or the like.

Figure 2:
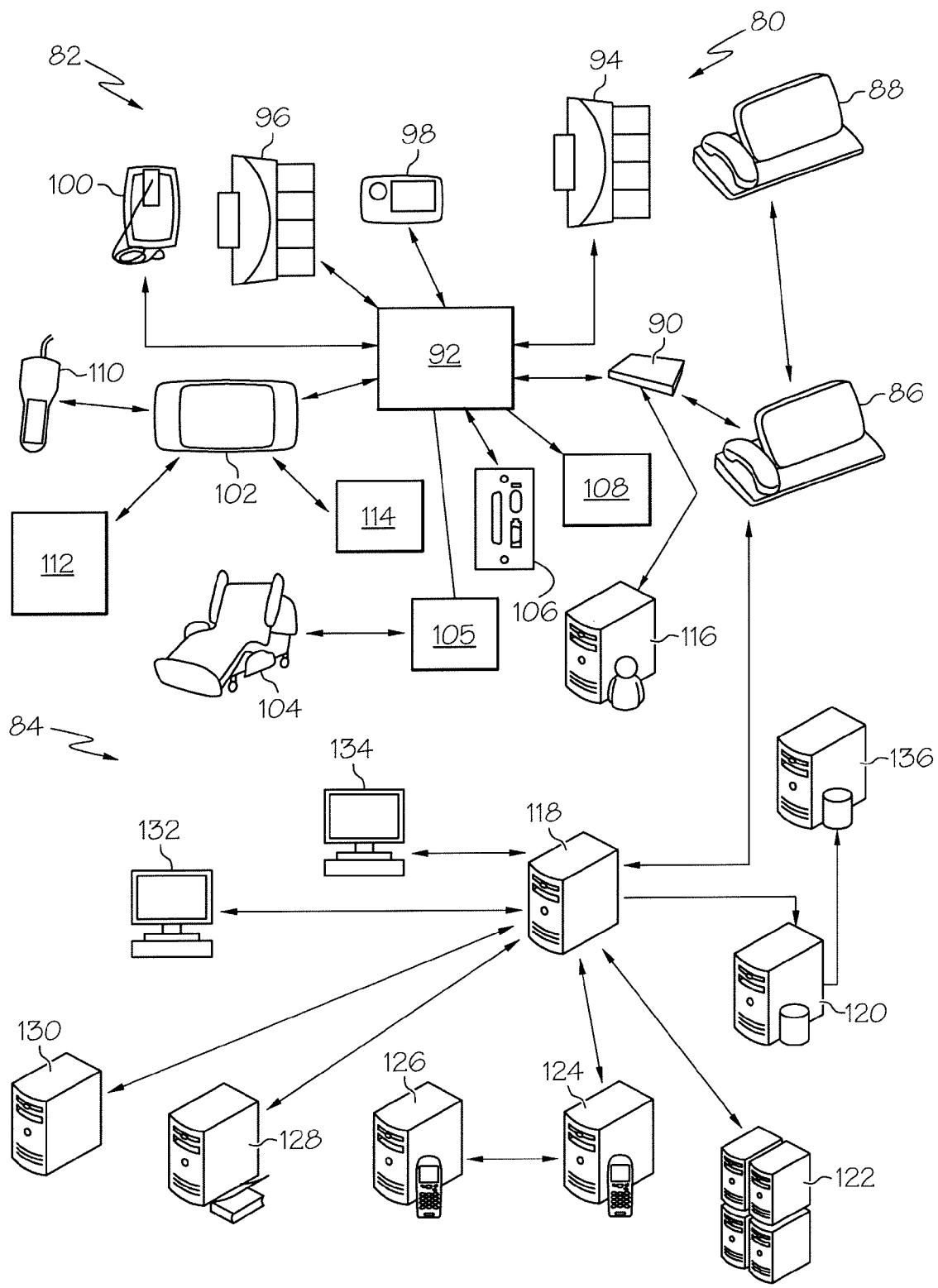
FIG. 2 is a simplified schematic showing physical components of a patient-nurse communication system including at least one indicator assembly, and showing connectivity to other services and systems.

FIG. 2 illustrates connectivity among components of an embodiment of a healthcare communication system 80 including a nurse call system 82 and a plurality of other services and/or systems 84. Nurse call system 82 includes a primary console 86 operably coupled to a switch 90, and a secondary console or station 88 logically coupled to primary console 86 and physically coupled to switch 90. Secondary console 88 is configured to display information about a nursing unit or unit(s) for which it is not the primary console.

Switch 90 is operably coupled to I/O board 92 and server 116. I/O board 92 is configured to receive incoming calls from a variety of devices connected thereto, including but not limited to indicator assemblies 94, 96, secondary console 98, call cord or switch 100, secondary console 102, bed 104, bed interface unit 106, remote locating receiver 108, and pillow speaker 110. In general, these devices are connected to I/O board 92 by an RS 485 link. Additional devices, such as bed connector 112 and call cord 114, may be coupled to or integrated with a secondary console such as console 102 and thereby connected to system 80. An interface 105 is operable to connect bed 104 to I/O board 92. In the illustrated embodiment, interface 105 is a 37 pin connector facing outward that a bed plugs into. On the other side of the plate 105, inside the back box, wires are connected to each pin of the 37 pin connector that could be run to other devices that the bed controls, such as lighting controller, TV, radio, and nurse call patient stations. It may be used in place of a bed interface unit or ASBC.

Server 116 is a VOIP server configured to translate system operations and communications to the corresponding messages that then control endpoint devices, such as nurse or staff stations, consoles or room input/output boards. As such, server 116 includes a soft telephony switch and other associated componentry. Server 116 may also provide integration with the hospital telecommunications structure (e.g., PBX or other voice communication system). In the illustrated embodiment, server 116 is a Windows server running 3CX.

Primary console 86 may optionally be coupled to a second server 118 by a network 115, such as a TCP/IP network. Server 118 may also be coupled to switch 90. Server 118 is similar to enterprise server 16 described above.

Other services and systems of system 84 are in communication with network 115 through server 118. Such other services or systems may include a database server 120, one or more third party servers 122, a first wireless communications server 124 for managing communications to and from wireless telecommunications devices, a second wireless communications server 126 for handling communications to and from wireless badges for locating and tracking of staff members, a user authentication server 128 for managing user accounts, passwords, and user authorization; a third party product integration server 130, which facilitates integration with third party or legacy products or services; a hospital administrative client 132 for conducting administrative tasks relating to patients and staff, such as adding patients and assigning staff to patients; and a status or reports server 134 for managing displays and reports of calls and notifications for one or more locations in the facility.

While the term "server" is used herein, it will be understood by those skilled in the art that the functionality represented or performed by these elements may comprise software programs or services that may be resident and/or executable by any computer, device or equipment in the system or more than one computer, device or equipment in the network.

In the illustrated embodiment, server 124 is configured to provide communication and configuration for wireless devices using Emergin Wireless Office; server 126 is configured to provide communication and configuration for wireless Vocera devices; server 130 is configured to interface with a Hill-Rom NaviCare system to receive and process alerts therefrom; and server 134 is configured to operate an "electronic status board," which displays locations within the facility and current information about them, such as active calls, bed status information, staff located in the location, and staff assigned to the location.

Figure 3:
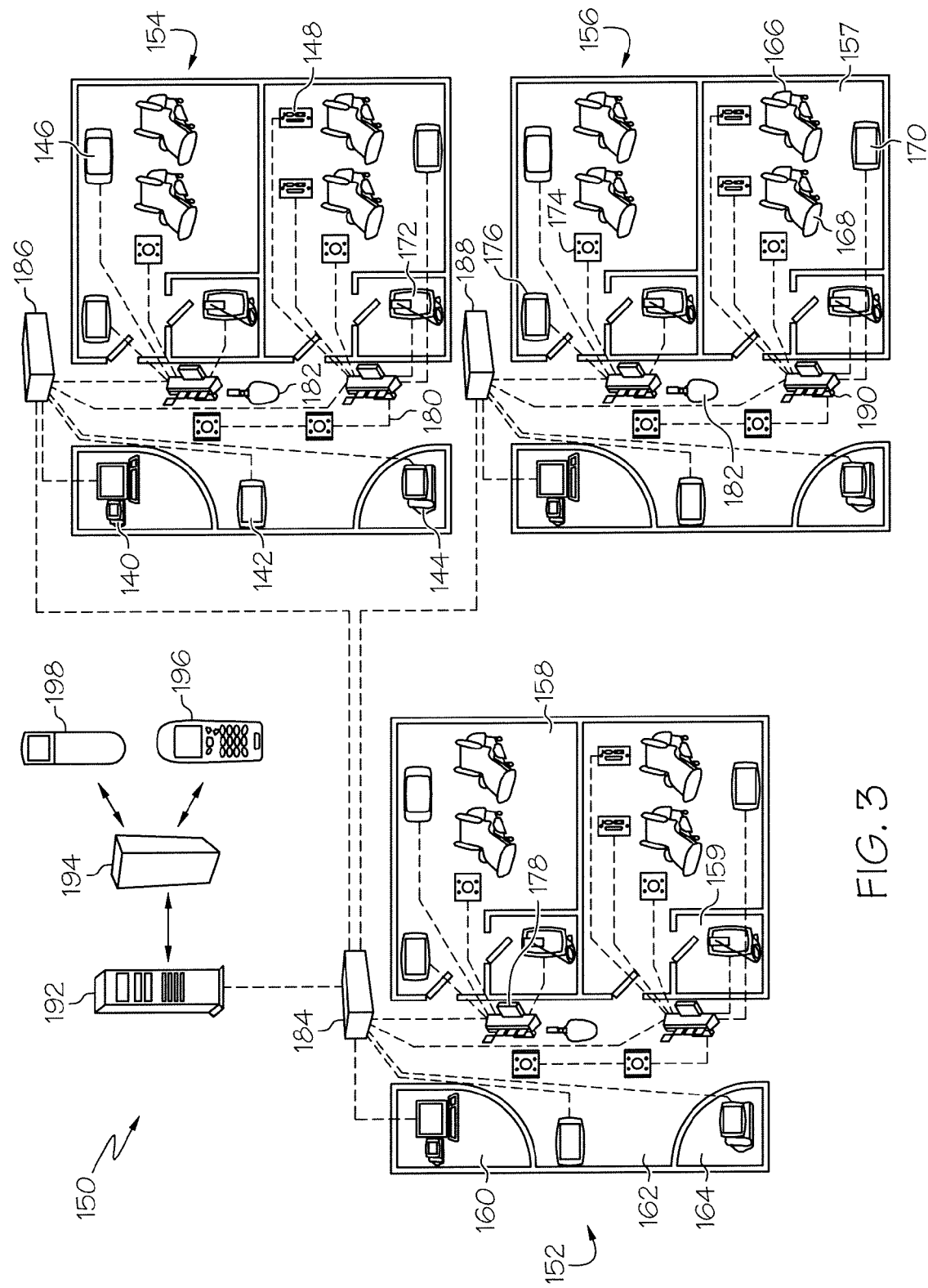
FIG. 3 is a simplified diagrammatic view of an exemplary implementation of a patient-nurse communication system in a patient care facility, including a plurality of indicator assemblies located throughout the facility.

FIG. 3 diagrammatically shows an illustrative implementation in a facility of a healthcare communication system 150 including many of the components described above. The illustrated facility has a plurality of nursing units or zones 152, 154, 156, each of which has one or more patient rooms or locations 158, hallways or common areas 138, and staff locations 160, 164. Each patient room 158 has a bathroom or washroom 159.

A number of call monitoring and/or communication or signaling devices are located throughout the facility, including primary consoles 140, secondary consoles 142, 144, 146, 170, 176, bed interface units 148 and beds 166, 168, toilet, bath and/or shower switches 172, wireless locating receivers 174, 180, and wireless locating transmitter badges 182. In the illustrated configuration, each nursing unit 152, 154, 156 includes a primary console 140, and each patient room includes at least one secondary console 146 and at least one switch 172 located in the bath/washroom 148.

An indicator assembly 190 is mounted in the hallway 138 outside of each patient room 158. Indicator assemblies 190 may be mounted either to a wall or ceiling, above the door to the room or in another suitable location indicative of the patient room with which the indicator assembly is associated. An I/O board 178 is also associated with each patient room and may be mounted adjacent to each indicator assembly.

While not shown, it will be understood that an indicator assembly may also or alternatively be located in a hallway or common area. For example, in L-shaped nursing units, an indicator assembly may be mounted on either side of the L so that a nurse in one part of the L can see a visual indicator relating to a patient in the other part of the L. Such and similar indicator assemblies may be referred to as "zone lights."

Secondary consoles 142, 144 may also be located in hallways 138 and staff locations 160, 164. Locating and tracking receivers 174, 180 are provided in the patient rooms 158, hallways 138 and other locations.

A POE switch 184, 186, 188 is associated with each unit 152, 154, 156 and operably coupled to the devices of its respective unit. System server 192 is coupled to switch 184, which is in turn coupled to switches 186, 188 in the illustrated embodiment. System server 192 is similar to server 118 described above. VOIP server 194 is operably coupled to server 192 and to telecommunications devices 196, 198, substantially as described above.

In operation, when a call or signal is initiated by one of the call initiating devices, executable computer logic processes the call or signal, determines which nurse or staff member to notify of the call, if a notification is necessary, locates the nurse or staff member, and routes an appropriate notification or notifications to one or more output devices associated with the assigned nurse or staff member or within the closest proximity to the assigned nurse or staff member. At the same time, a notification is routed to the output device nearest the location where the call originated. Such computer logic may be located in memory at a primary console, I/O board or at the application server 192.

For example, if a nurse is assigned to units 152 and 156, is currently tending to a patient in room 157 of unit 156, and a patient or piece of monitoring equipment in room 158 issues a call, then system 150 locates the nurse using room receivers 174 and hall receivers 180 and the nurse's badge 182. System 150 then activates the appropriate visual and/or audible notifications at the indicator assembly 178 assigned to the patient room where the call originated. System 150 may activate a visual and/or audible notification at the console 170, nearest the nurse's location, as well. System 150 may cancel or disable one or more of the notifications when the locating receivers detect that the nurse has departed the area or when the nurse enters the room 158 where the call originated.

Additional details describing the structural components, connectivity, functionality, and other operations of the above-described communication systems 10, 80, 150 may be found in the U.S. Provisional Patent Application entitled DISTRIBUTED HEALTHCARE COMMUNICATION SYSTEM, filed on the same date as the present application and incorporated herein by reference.

Various embodiments of an indicator assembly suitable for use in a healthcare communication system such as described above and in the related applications, which are incorporated herein by reference, are shown in FIGS. 4-20 and described below.

Figure 4:
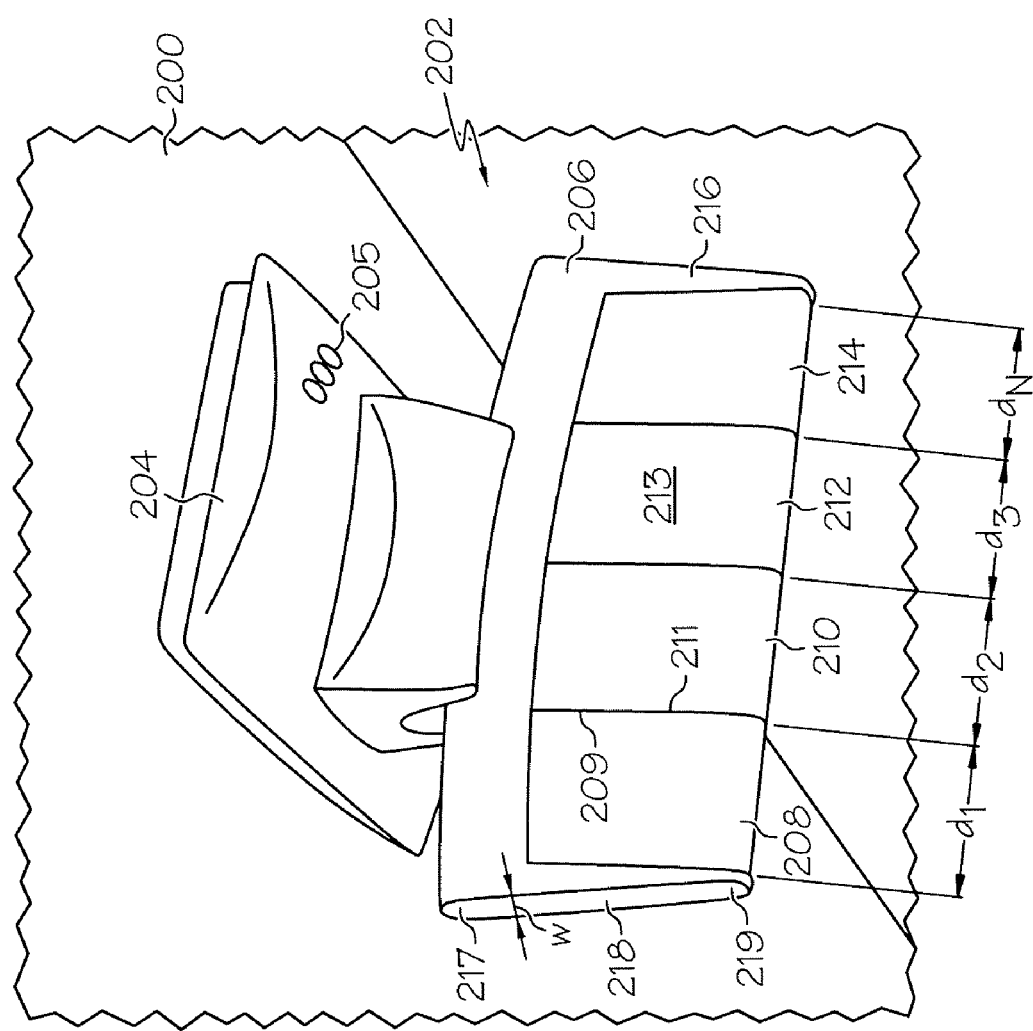
FIG. 4 is a perspective view of an indicator assembly for a patient-nurse communication system illustrating a horizontally oriented ceiling mounting.

FIG. 4 shows an indicator assembly 202 mounted to a ceiling 200 in a horizontal orientation. Indicator assembly 202 includes a base 204 configured to mount the assembly 202 to a wall or ceiling, a housing 206 coupled to the base and a plurality of visual indicators 208, 210, 212, 214 coupled to the housing 206. Each arm 216, 218 has a width "w" along the distance from its first end 217 to its second end 219. In the embodiment of FIG. 4, the width "w" is about the same along the length of each arm and the width of arm 216 is substantially the same as the width of arm 218.

Indicators 208, 210, 212, 214 are horizontally aligned and positioned side by side between arms 216, 218 when assembly 202 is mounted to a ceiling. Indicators 208, 210, 212, 214 are vertically aligned one on top of another between arms 216, 218 when assembly 202 is mounted to a wall. As a result of the adjacent positioning of the indicators 208, 210, 212, 214, the distance $d_T$ from the first end of the first indicator 208 to the second end of the last indicator 214 in the assembly 202 is substantially equal to the sum, over all of the indicators in the assembly 202, of the individual distances $d_1$, $d_2$, $d_3$, $d_N$ across each individual indicator. For example, the second edge 209 of the first indicator 208 generally abuts the first edge 211 of the second indicator 210, and so on.

Each indicator 208, 210, 212, 214 is substantially quadrilaterally shaped and has a thickness that is substantially the same or less than the width w of the opposing arms 216, 218 and substantially uniform throughout. In addition, each of the indicators 208, 210, 212, 214 has substantially the same thickness and other dimensions as the other indicators. Further, although not shown, it will be understood that each indicator 208, 210, 212, 214 has two opposing sides, such that visual notifications can be seen from either direction in a hallway.

A light source, such as a plurality of multi-color LEDs, is mounted inside housing 206 such that each indicator 208, 210, 212, 214 is configured to selectively illuminate in one of a plurality of colors in response to a call received from a healthcare communication system. Each indicator 208, 210, 212, 214 may also be individually configured to support an icon indicative of a patient location or condition or other healthcare-related need. Such icons may be printed on a clear or transparent film with adhesive backing and adhered to each opposing face or surface 213 of each indicator. As such, indicator assembly 202 may display visual notifications that include one or more colors, one or more icons, or a combination of colors and icons. A speaker (not shown) and speaker grille 205 may also provided in housing 205 to provide audible notifications in addition or alternatively to the visual indications. Computer logic of the healthcare communication system determines which combination of indicators, color, icon, and sound to activate in response to a particular call. Since the assembly 202 is either horizontally or vertically mountable, in the embodiment of FIG. 4 any icons to be used are selected and installed after the mounting orientation has been determined.

Figure 5:
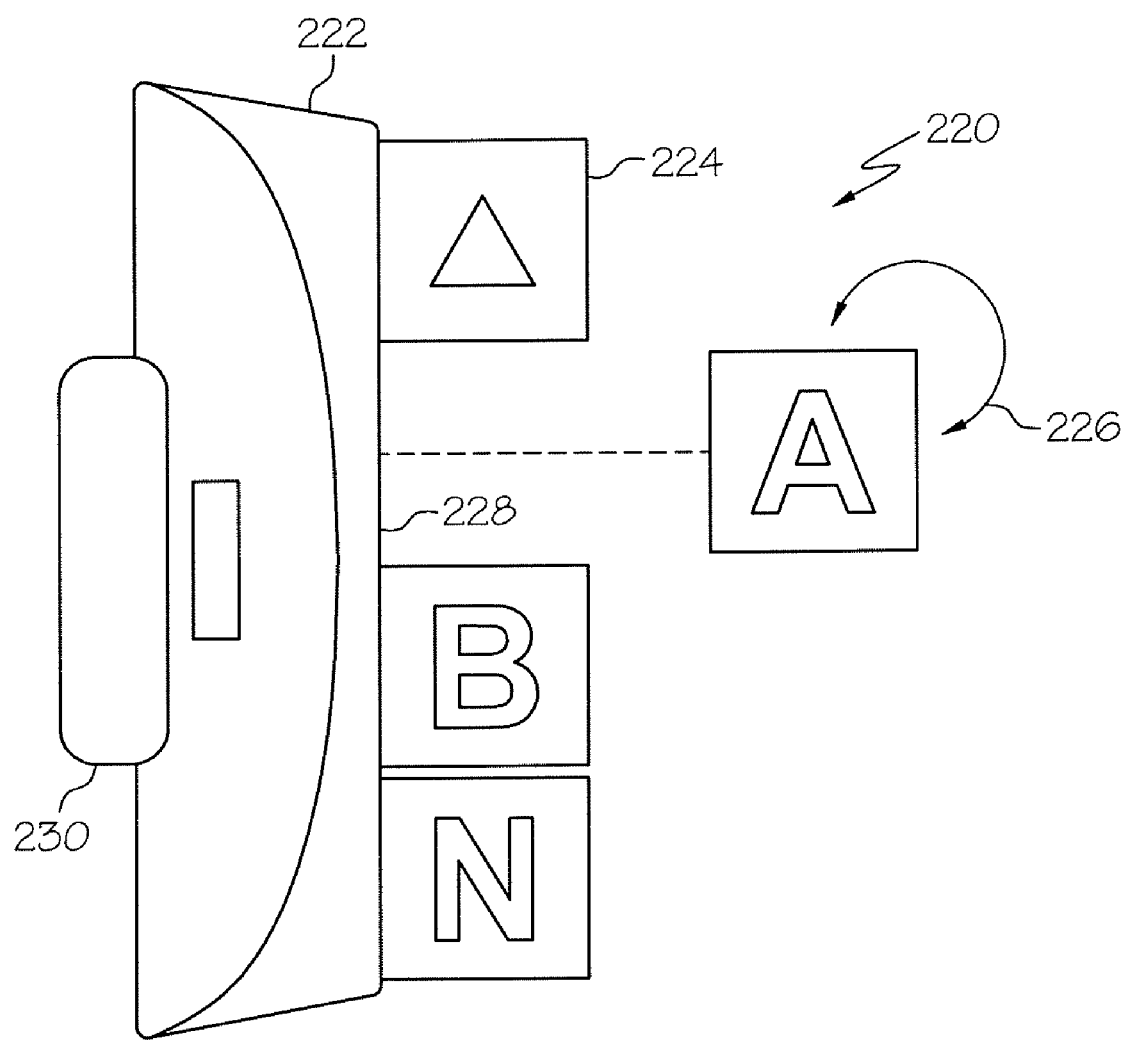
FIG. 5 is a side view of an indicator assembly in a vertical orientation, including horizontally and vertically configurable icons, and showing an electronic assembly adjacent thereto.

FIG. 5 shows another embodiment of an indicator assembly 220 mounted to a wall in a vertical orientation, and an electronic assembly or input-output board 230 integrated therewith. Indicator assembly 220 includes a housing 222 and a plurality of configurable indicators 224 insertable into a longitudinal slot 228. Indicators 224 may be configured to display icons. Slot 228 and indicators 224 are configured such that indicators 224 are individually removable from the slot 228 and may be inserted in the slot 228 in either a first orientation suitable for vertical or wall mounting of the assembly 220 or a second orientation suitable for horizontal or ceiling mounting. As shown by arrow 226, in the illustrated embodiment, the first or the second orientation is selected by rotating the indicator 224. Electronic assembly 230 may be installed within the housing 222 or may have a separate housing mounted adjacent assembly 220.

Figure 6:
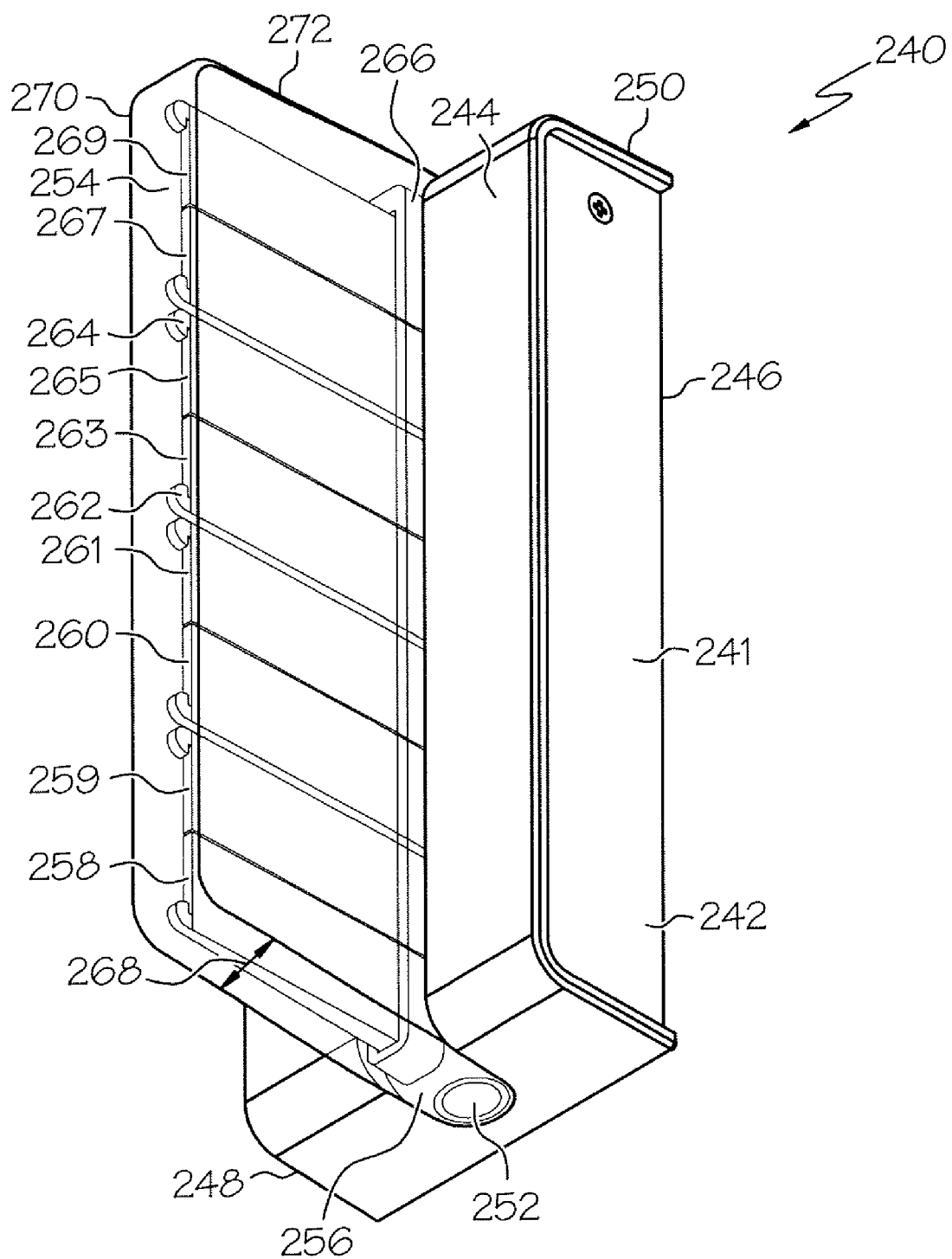
FIG. 6 is a perspective view of an assembled indicator assembly including a plurality of light guides.
Figure 7:
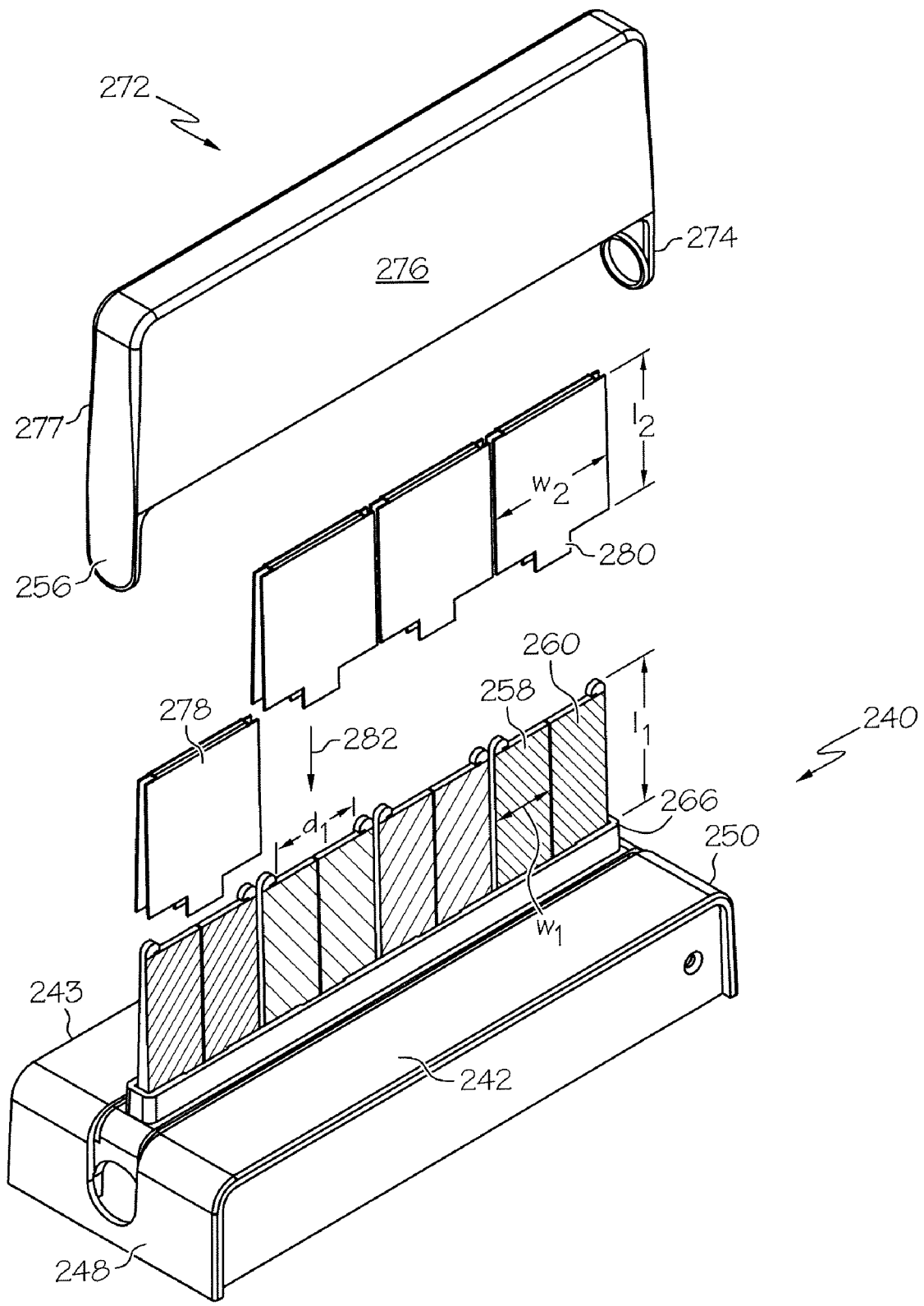
FIG. 7 is an exploded perspective view of components of the indicator assembly of FIG. 6, including a cover, one or more icons, light guides and an indicator housing.

FIGS. 6-7 illustrate aspects of another indicator assembly that is either vertically or horizontally mountable. Indicator assembly 240 has a housing 241, which has first and second longitudinal sides 242, 243 that are laterally spaced by first and second ends 248, 250. Housing 241 also has a top portion 244 and a bottom portion 246. Bottom portion 246 is mountable to a surface, such as a wall or a ceiling. Top portion 244 includes a longitudinal mounting portion or slot 266 configured to support a plurality of adjacently positioned visual indicators or light guides 258, 260 along the longitudinal length of the housing 241. Ends 248, 250 each have a slot 252 configured to receive an arm 256 of a cover 272, which slides over the light guides 258, 260 and arms 256 slide, snap or lock into slots 252.

Cover 272 has a thickness 268, defined by the distance between opposing faces 276, 277. Thickness 268 is substantially uniform along the top 270 and arm portions 256, 272. As such, faces 276, 277 are substantially parallel to each other. Cover 272 has a length that substantially corresponds to the longitudinal length of the housing 241. As such, the thickness 268, the longitudinal length of the housing 241, and the length of the arms 256, 272 substantially define the interior volume of the cover 272.

Figure 20:
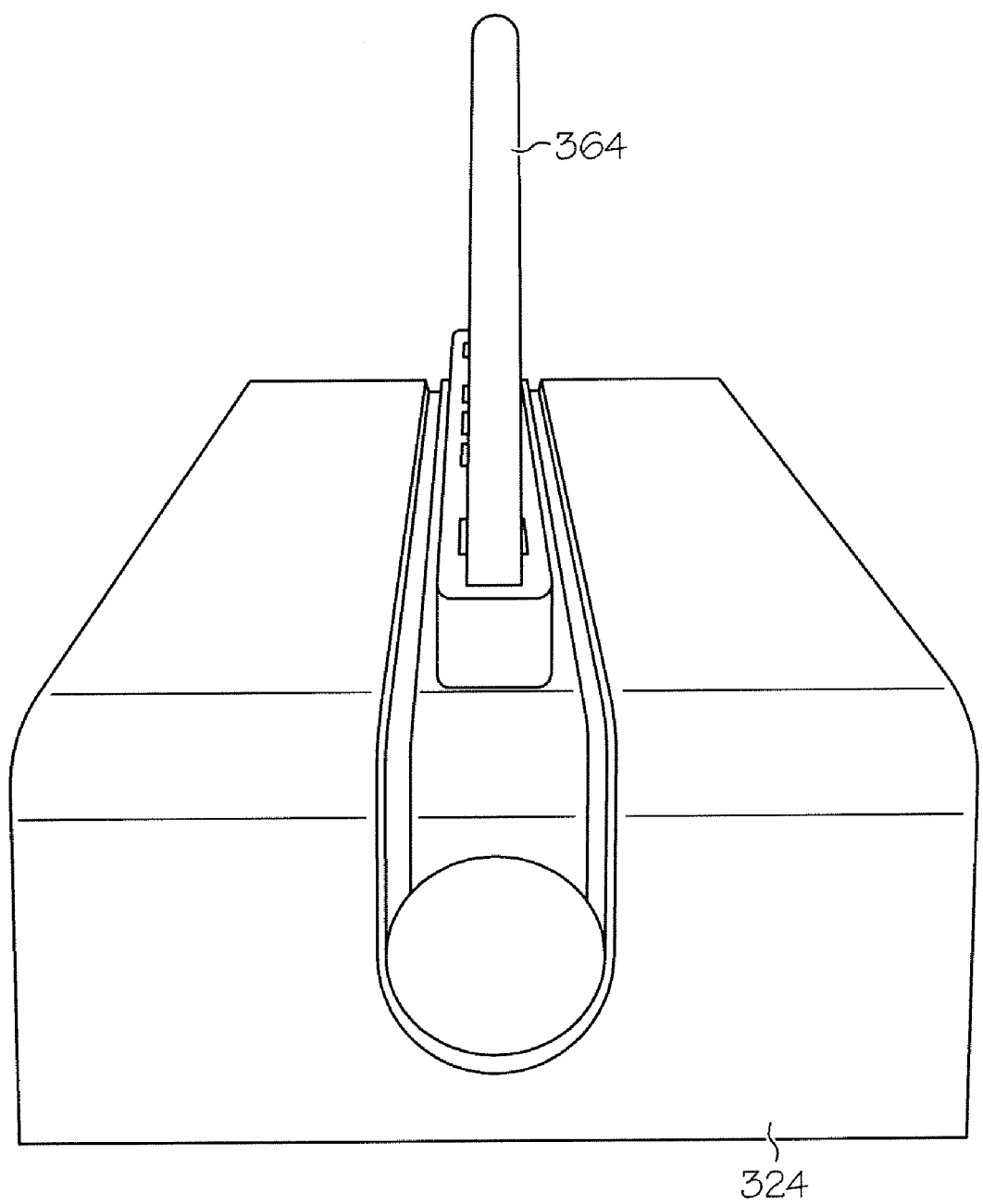
FIG. 20 is a side perspective view of an indicator assembly showing a light guide having a wedge-like shape.

Light guides 258, 259, 260, 261, 262, 263, 265, 267, 269 are positioned adjacent one another in a line and are substantially identically shaped. In the illustrated embodiment, each light guide 258, 259, 260, 261, 262, 263, 265, 267, 269 is wedge-shaped, with the thickness at its top end, closest to the cover, being less than its thickness at its bottom end, closest to the housing. FIG. 20 illustrates an example of a wedge-shaped light guide. The length $l_1$ of the light guides is less than the height of the cover 272 and the largest thickness of the light guides is less than the thickness 268 of the cover. Moreover, in the illustrated embodiment, the thickness of each of the light guides is less than its length $l_1$ and is also less than its width $w_1$. Further, the dimensions of each light guide are substantially the same as the dimensions of the other light guides.

However, in the illustrated embodiment, the difference between the thickness of the light guide at the top end and the thickness of the light guide at the bottom end is a relatively small difference. In one embodiment, there is about a 2 millimeter difference between the top end thickness and the bottom end thickness (i.e., the top end thickness is in the range of about 2 millimeters and the bottom end thickness is in the range of about 4 millimeters). At the top end, the thickness may range from zero (i.e., creating a point or edge at the top end) to slightly less than the bottom end thickness. At the bottom end, the thickness may be substantially determined by the configuration of LED(s) that are used. For example, a greater bottom end thickness may require multiple LEDs to illuminate the entire light guide. Where a single LED is used to illuminate each light guide, as in the illustrated embodiment, a thinner bottom end thickness may be configured to conform to the dimensions of the LED. For example, the bottom end thickness of the light guide may be substantially equivalent to the width of the LED.

Figure 19:
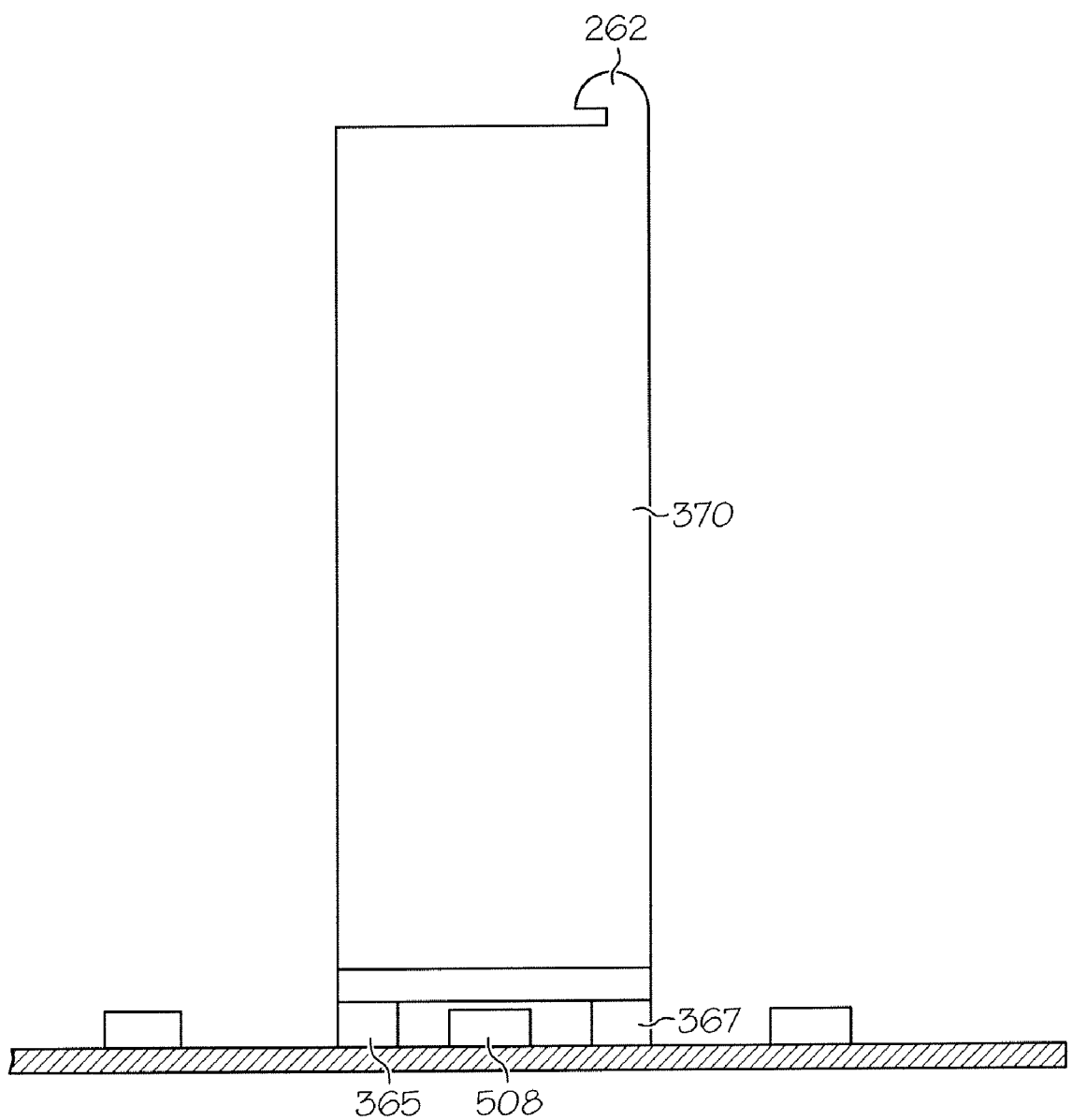
FIG. 19 is a front perspective view of an indicator assembly showing the arrangement of light guides and LEDs relative to the housing.

FIG. 19 shows the relative positioning of the light guides and the LEDs in the indicator assembly, while FIG. 20 shows a side view illustrating the elongated edge of the light guide. The two opposing faces of each light guide have a texture or a surface material that is configured to disperse the light more consistently across the entire face. The two opposing elongated wedge-shaped edges each have a coating that prevents light from one light guide from bleeding over to the adjacent light guides. In the illustrated embodiment, the coating includes a hot stamp reflective foil. In general, it is a separate reflective material that applied to the light guide with a hot stamping process.

In the illustrated embodiment, light guides 258, 260 are arranged in pairs. Each light guide in a pair has an ear or shoulder 262, such that pairs of light guides 258, 259; 260, 261; 263, 265; 267, 269 have opposing ears or shoulders, i.e., 262, 264. Ears or shoulders 262,264 extend upwardly from the light guides toward the top 270 of the cover and may be provided to guide the placement of icons on the light guides.

Each light guide may be individually configured and controlled by circuitry provided within the indicator assembly in response to signals received from a nurse or staff station, an input-output board or another component of a healthcare communication system. Each light guide may be individually illuminated in a different color by a light source mounted in the housing 241, or multiple light guides may be illuminated in combination to create another form of indicator. The illustrated embodiment 240 includes four pairs of light guides resulting in eight individual visual indicators and, in when used combination with multi-color LEDs, has a potentially unlimited number of possible visual notifications by varying the colors that are turned on or off and/or varying the intensity of the light provided by one or more of the LEDs.

Figure 13:
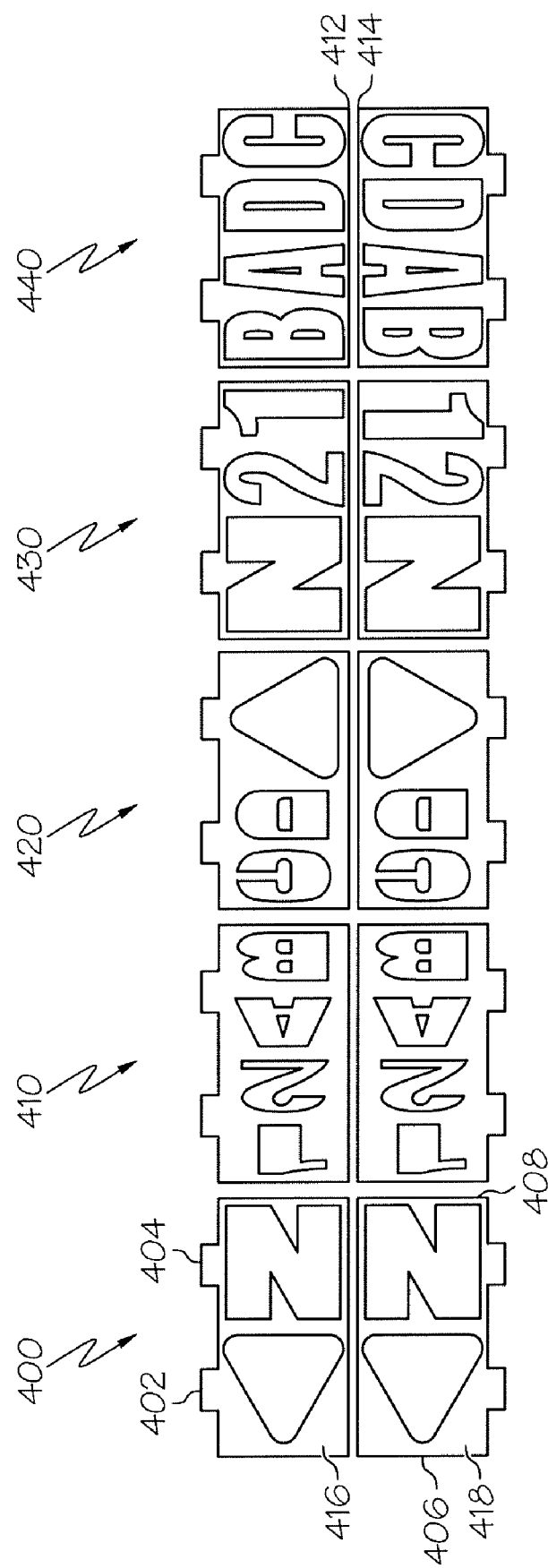
FIG. 13 illustrates exemplary icons for an indicator assembly.

In the illustrated embodiment, each light guide or lens 258, 259; 260, 261; 263, 265; 267, 269 is a solid plastic piece. Each label or sleeve 278 is configured to fold or slide over the opposing faces of the light guides in the light guide pair. As such, the icon sleeve 278 has a width substantially the same but sufficiently less than the pair of light guides that the icon 278 fits within the area defined by the light guide pair. In other words, the length $l_2$ of the icon 278 is about the same as the length $l_1$ of the light guide, but the width $w_2$ of the icon 278 is about the same as two times the width $w_1$ of the light guide. Ears 262, 264 help guide the icon 278 as it is installed onto the light guides. Each icon 278 has an alignment tab 280 that aligns with the central portion of the light guide. Icons can be customized according to the needs or preferences of the facility. Example icons are shown in FIG. 13 and described below. While the figures show icons that cover the area of two light guides, smaller icons that fit on single light guides, or larger icons that fit on more than two light guides, may also be used.

Figure 8:
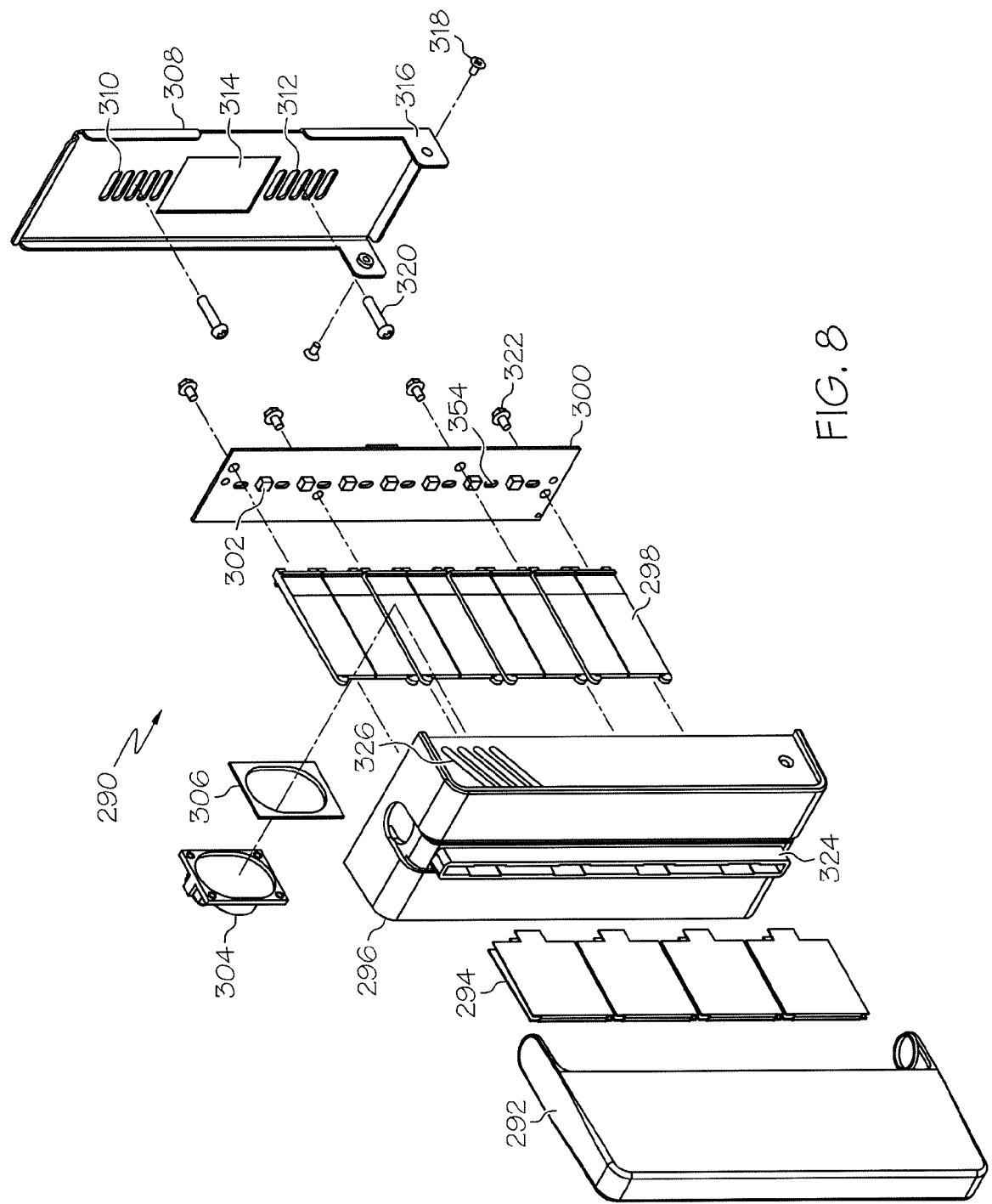
FIG. 8 is an exploded front perspective view showing components of an indicator assembly including a speaker, light guides, and a printed circuit board assembly including light guides mounted thereto.

FIG. 8 shows an exploded view of an indicator assembly 290 similar to the embodiment of FIGS. 6-7. Assembly 290 includes a mounting plate 308, a printed circuit board assembly 300, a light guide assembly 298, a housing 296, an icon assembly 294 and a cover 292. Mounting plate 308 includes a pair of longitudinally spaced mounting portions 310, 312, an aperture 314 located between the mounting portions 310, 312, and a pair of ears 316. Ears 316 are coupled to an end of housing 296 via screws or similar suitable fasteners.

Circuit board assembly 300 includes a plurality of longitudinally spaced tri-color LEDs 302 and a plurality of longitudinally spaced mounting ports 354 configured to receive mounting pins or "feet" (e.g., 365, 367, 369) of the light guides in the light guide assembly 298. LEDs 302 and slots 354 are substantially centrally located on the board 300 and arranged in a line in an alternating fashion along the longitudinal length of the board 300. LEDs 302 are positioned to align with the central portion of each respective light guide and slots 354 are located to align with the light guide mounting pins, which are spaced from the central portion of the light guide. Feet (e.g. 365, 367, 369) each have a length that is slightly longer than the height of the LED such that there is only a very small gap between the surface of the LED and the bottom edge of the light guide.

Board 300 also includes circuitry to connect the multimedia microprocessor of an input-output board, described above, to speaker 304 to enable a variety of sounds including sound recordings, such as .wav files, to be output from speaker 304. Speaker 304 is mounted to the interior region of the housing 296, adjacent the speaker grille 326, by speaker mount 306. Mount 306 is a foam piece with adhesive on both sides.

Housing 296 includes a longitudinal slot 324 and light guide assembly 298 extends upwardly out of slot 324 as described above. Icons 294 are made of semitransparent or clear film made of polycarbonate such as Lexan or a similar suitable material. The iconic indicators may include alphanumeric characters, symbols, or graphics, and may be applied to the film with a matte finish. Icons 294 have an adhesive backing so that they may be applied to the opposing faces of the light guides. Cover 292 slides over the light guide-icon assembly and connects with housing 296 as described above. Cover 292 is a clear plastic housing made using PC/ABS or similar suitable material.

Figure 9:
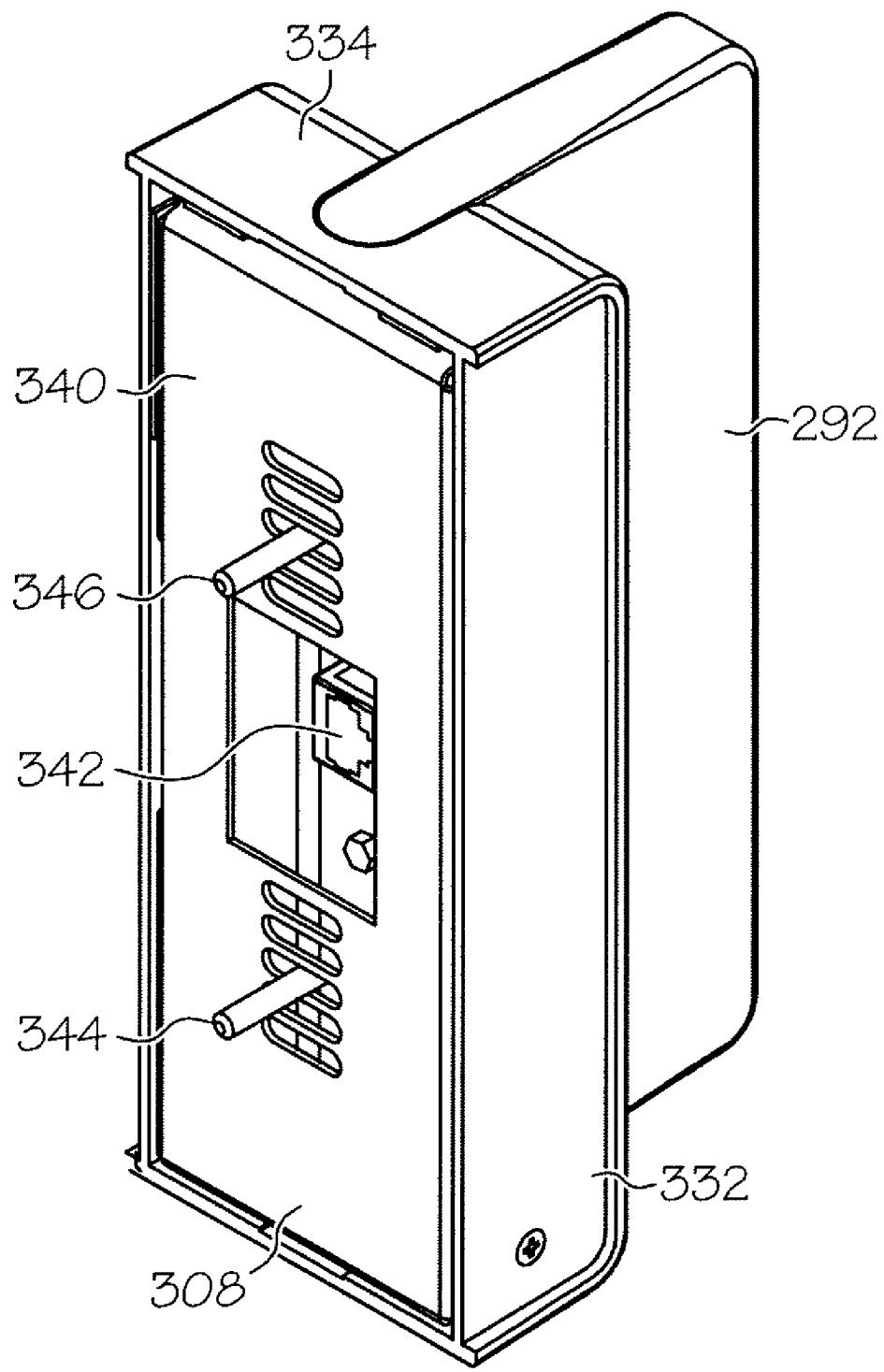
FIG. 9 is a rear perspective view of the indicator assembly of FIG. 8, showing a rear portion of the housing including a plurality of configurable mounting ports, mounting screws and a connectivity port.

FIG. 9 shows a rear perspective view of indicator assembly 290, including cover 292, first end 334 and first side 332 of housing 296, and mounting plate 308. Mounting plate 308 is adaptable to mount to a variety of different backboxes or gangboxes, including but not limited to 1-gang, 2-gang, 3-gang and 4-gang boxes. As such, mounting regions 310, 312 each include a plurality of mounting ports or apertures through which mounting pins or screws 344, 346 are inserted to connect the mounting plate 308 to a backbox or other suitable mounting structure, which is installed in a wall or ceiling of a facility. Through aperture 314 the communications port 342 is shown. Communications port 342 is coupled to circuit board 300 and extends outwardly from the rear side of the circuit board toward the mounting plate 308. Communications port 342 operably couples indicator assembly 290 to an electronic assembly for two-way communication of data and/or instructions and, optionally, power as well. In the illustrated embodiment, an RJ45 connector is used to provide power, data and instructions, including sound (i.e., streaming audio) when an audible indicator is to be activated at the assembly 290.

Figure 10:
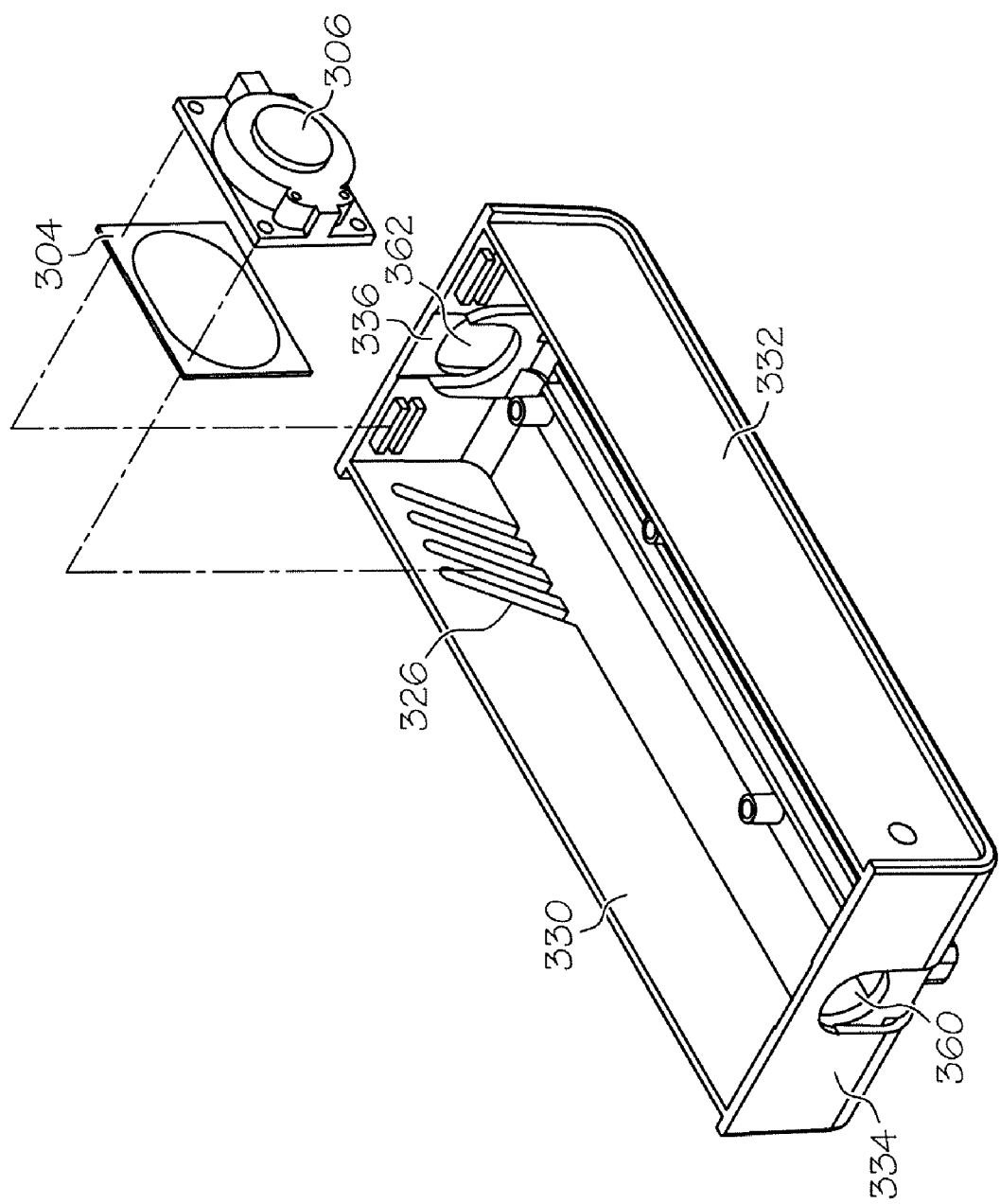
FIG. 10 is an exploded perspective view of a portion of the indicator assembly, showing a portion of the housing and speaker components.

FIG. 10 shows a perspective view of an interior region of housing 296 including laterally spaced side walls 330, 332 and longitudinally spaced ends 334, 336. Each end 334, 336 has an aperture 360, 362 configured to receive a connector portion of cover 292. Speaker 306 is mounted to the interior side of wall 330 adjacent speaker grille 326 via speaker mount 304 as described above.

Figure 11:
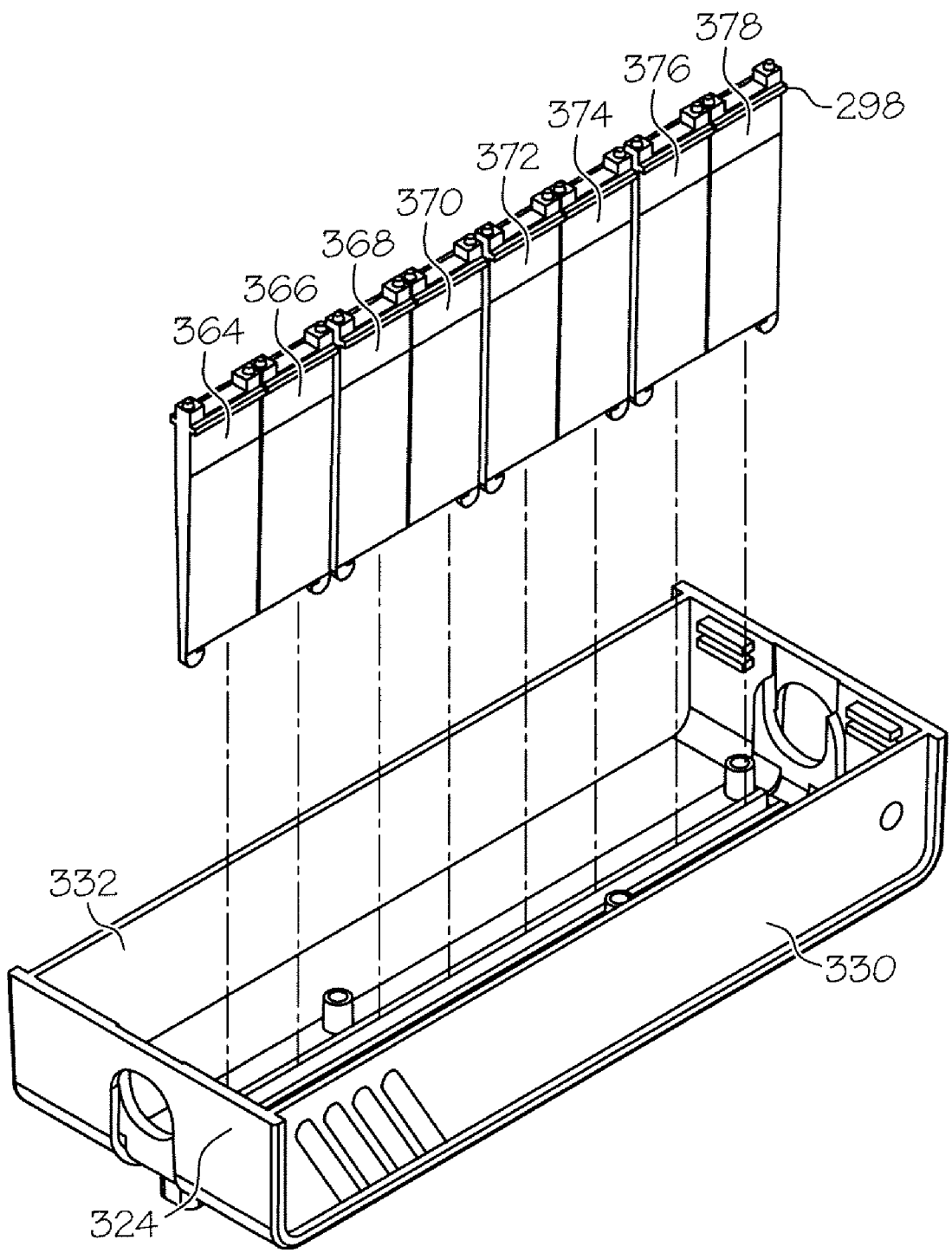
FIG. 11 is an exploded perspective view of a portion of the indicator assembly, showing a portion of the housing and the light guides.
Figure 12:
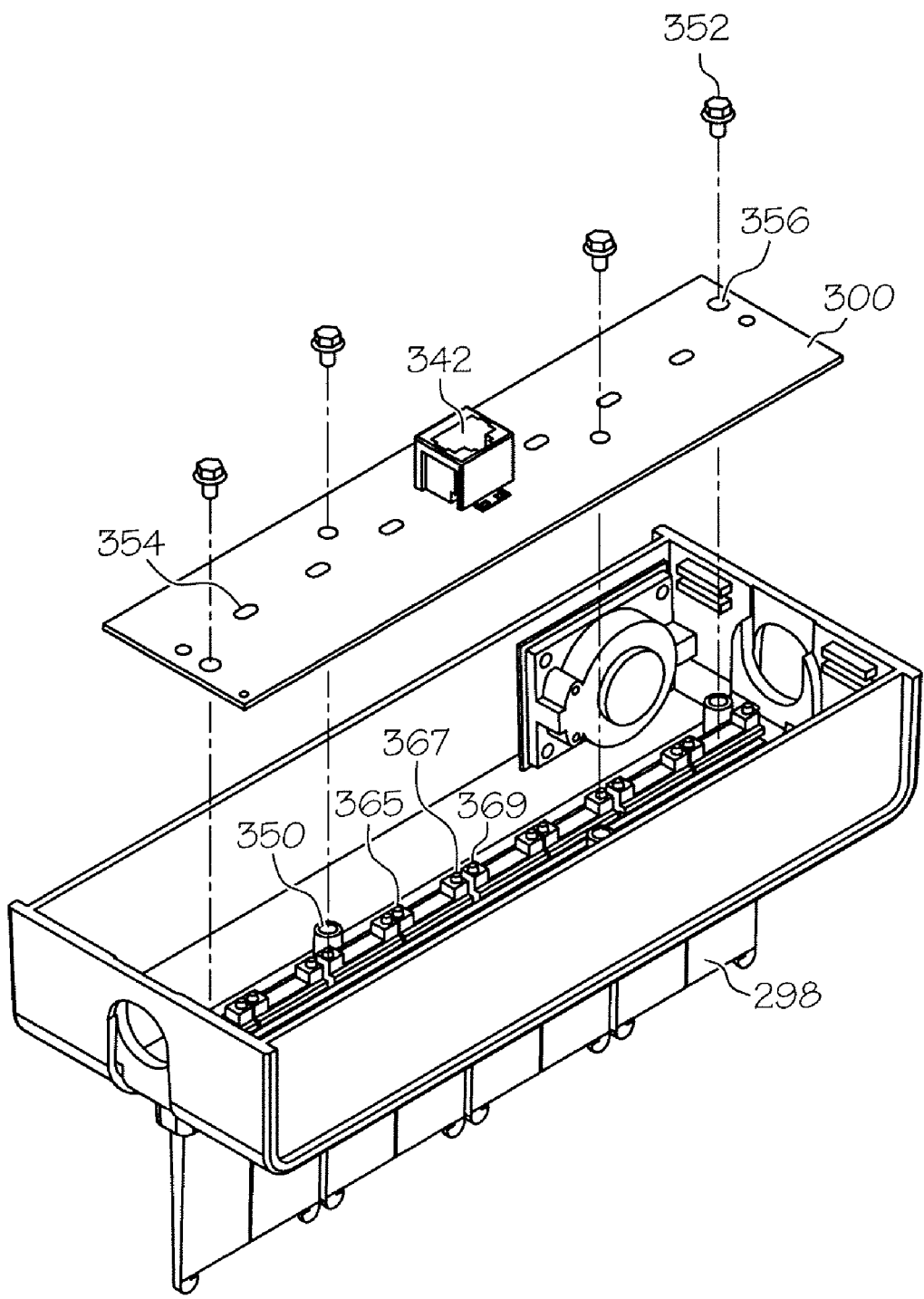
FIG. 12 is an exploded perspective view of a portion of the indicator assembly showing a printed circuit board assembly including alignment slots for the light guides.

FIGS. 11-12 shows individual light guides or lenses 364, 366, 368, 370, 372, 374, 376, 378 of light guide assembly 298 aligned with longitudinal slot 324 of housing 296. Each light guide or lens is a solid plastic piece made of clear polycarbonate plastic or similar suitable material. Each light guide has a pair of feet or pins (e.g. 365, 367) that insert into holes (e.g. 354) in the circuit board 300 so that an LED, which is perpendicularly mounted to the circuit board, is positioned below or underneath the bottom portion of the light guide and in the middle of the light guide, i.e. about half-way between the light guide feet. In other words, each light guide is positioned above a perpendicularly mounted LED so that the LED is aligned with the central portion of the light guide or lens. The light travels from the LED into the edges of the light guide/lens and through the light guide/lens. The wedge-like shape of the light guide/lens is configured so that some of the light hits both faces of the lens. Each face of the light guide/lens has a texture or special material that scatters the light so that it is evenly dispersed within the light guide.

FIG. 12 illustrates installation of circuit board 300 into housing 296 after light guide assembly 298 has been inserted into the longitudinal slot. Circuit board 300 is positioned so that each hole 354 is aligned with a pair of adjacent light guide feet (e.g., 367, 369). Also, mounting holes (e.g, 356) of circuit board 300 align with respective mounting ports (e.g., 350) of the housing 296 so that fasteners (e.g., 352) may be installed therein.

FIG. 13 illustrates exemplary icon labels or sleeves, which may be used in connection with the indicator assembly. In the illustrated embodiment, labels or sleeves 400, 410, 420, 430, 440 are semi transparent film and adhere to the opposing faces or sides of the light guides, however, it will be understood that other methods of installation may be used. Each label 400, 410, 420, 430, 440 includes alphanumeric characters, symbols or graphics, or a combination of any of these, which are configured for vertical or horizontal alignment of the light guide as shown. Each label set 400, 410, 420, 430, 440 has a plurality of labels that have two sides 416, 418 and a pair of fold lines 412, 414 such that the portion of the label between the fold lines adheres to the top portion of the light guide and the sides 416, 418 fold over and adhere to the respective sides of the light guides. As such, the labels are folded, molded or otherwise adapted to conform to the shape of the light guides, which, in the illustrated embodiment, is a wedge-like shape as shown, wherein the thickness at the top of the light guide (closest to the top of the housing) is smaller than the thickness at the bottom of the light guide (closest to the circuit board).

Tabs 402, 404 generally align with the junction or point where two light guides in a pair abut each other. The labels may have a greater or lesser number of tabs. For example, each label may have two tabs (for a total of four tabs per label set), with each tab being configured to align with the center of a light guide.

In the illustrated embodiment, label set 400 includes two labels 406, 408 that each have one icon (a triangle and an "N"). Since these icons are larger in size, they each extend across the width of two adjacent light guides, so that the label set 400 extends across four light guides when installed as a unit. Any of the label sets may be divided into individual labels that are installed separately instead of as a unit. Other labels, such as label sets 410 and 440, include multiple icons on each label for a configuration of one icon per light guide. Other labels, such as labels 420 and 430, have a combination of larger icons that span two light guides and smaller icons that span one light guide.

In one embodiment, indicator assembly 290 is IBM Part No. 43T1899. One embodiment of a suitable electronic assembly for use in connection with the described indicator assemblies is IBM Part No. 43T2063.

Figure 14:
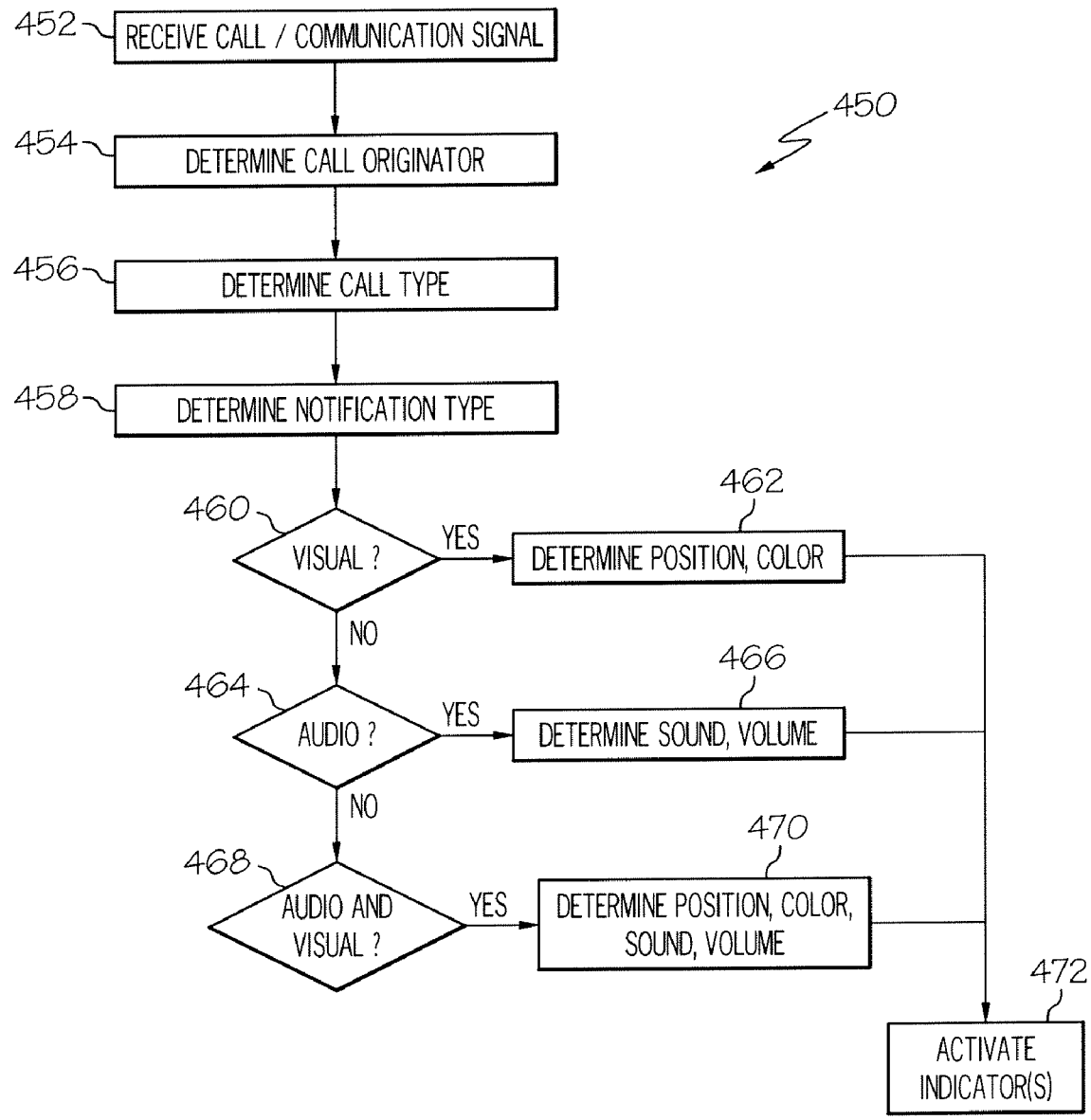
FIG. 14 is a flow diagram of operations executable by a computer processor to control operation of an indicator assembly in response to signals received from a nurse-patient communication system.

In operation, computer program logic is configured to determine whether, when and how to activate an indicator assembly. FIG. 14 illustrates operations executable by computer or processor circuitry to control the operation of an indicator assembly of the type described herein. At functional block 452, a call or communication signal is received by the healthcare communication system, indicating the occurrence of an event, request, or condition relating to a patient in the healthcare facility. The call or signal may be received or detected by a computer or computing device connected to the healthcare communication system network. For example, in the illustrated embodiment, the I/O board that is assigned or associated with the room from which the call initiated will receive the call and send control signals to the indicator assembly assigned or associated with that room to activate the appropriate visual and/or audible indicators.

At functional block 454, computer programming logic determines the origination of the call or communication. The call origination information includes an indicator of the location placing the call, i.e., a patient room. The call origination information may also include information identifying the particular call device in the room from which the call initiated, i.e., the shower, bathroom, bed, or staff station.

At functional block 456, computer programming logic determines the type of call that was received. The call type may be, for example, "emergency", or "normal." Alternatively or in addition, a number of different call types may be used that indicate additional details about the call. For example, smoke alarm call, Code Blue emergency call, staff emergency call, call from patient shower or bath, call from patient bed, call from visitor station, etc. It should be noted that indicator assemblies, in addition to outputting notifications relating to incoming calls, can also be originators of calls. For example, if an indicator assembly has a malfunction or failure, such as an LED failure, the indicator assembly will issue a call to the healthcare communication system and an appropriate notification will be generated in response to the call.

A priority level may be associated with each call type and/or call originator. The priority type may be used by the computer program logic to resolve which call of more than one should be handled first. For example, emergency calls may have a higher priority than non-emergency calls. Computer program logic will then cause the notifications for higher priority calls to be output (i.e. displayed and/or sounded) first.

At functional block 458, computer program logic determines the type of notification that needs to be output based on the call parameters such as call originator, call type and call priority. Indicator assemblies of the type described herein are configured to provide visual and/or audible notifications. Accordingly, at functional blocks 460, 464, 468, computer program logic determines whether, based on the call parameters, a visual, audio, or combination of visual and audio notification is to be output at the indicator assembly. If a visual notification is to be displayed, at function block 462, computer program logic determines which position or positions on the indicator assembly should be illuminated and the illumination color. A position may correspond to one or more light guides in the indicator assembly. For example, each light guide in an indicator assembly may be uniquely numbered with a position number. Computer program logic will then send the appropriate control signals to the indicator assembly closest to the patient location to cause the appropriate visual indicator(s) to be activated at functional block 472.

If an audible notification is to be sounded, at functional block 466 computer program logic determines which sound to be played. For example, each available audio file may be uniquely numbered with a file number. Computer logic may also be executed to set a specific volume level for the audio to be played at. For example, emergency notifications may be configured to be played at a louder volume than normal notifications. Computer program logic will then send the appropriate control signals to the indicator assembly closest to the patient location to cause the appropriate audible indicator(s) to be activated at functional block 472. If a particular call requires a notification including both a visual indicator and an audible indicator, then both of the processes 462, 466 will be executed at functional block 470 to determine the appropriate control signals, and the appropriate visual and audio indicators will be activated at functional block 472. In the illustrated embodiment, the above described computer logic is executed at the I/O board nearest the location of the call originator.

Table 1 below contains examples of types of visual and audible indicators that may be output to an indicator assembly as part of the operation of the patient-nurse communication system.

TABLE 1

| Call Type | Call Originator | Indicator Location | Visual Notification(s) | Audible Notification |
|---|---|---|---|---|
| Code Blue Call | Patient Bed | Room 100, Bed A | Bed A, fast flash red triangle | File1.wav, loud volume |
| Normal Call | Staff console | Room 212, Bed B | Bed B, solid | File2.wav, normal volume |
| Emergency Assist | Lavatory Switch | Room 105, Bed A | Bed A, solid, slow flash triangle | File3.wav, loud volume |

It should be noted that notifications may be output at other devices in addition to the indicator assemblies. For example, a visual notification may be displayed on a display screen of a primary or secondary station or console that is connected to the healthcare communication system, and/or an audible notification may be played at the station or console.

The notifications are configurable according to the facility's needs or preferences. In the illustrated embodiment, configuration information is stored in a computer-accessible medium such as a database, and may be changed or updated via a user interface of a primary station or console, by an authorized user. The configuration information includes a list of "call" (alert) types that can be generated by a user. Call types include code blue, staff emergency, patient normal call, etc. as described above. Associated with each call type in the list are parameters that tell the system what light guides to illuminate on the dome light as well as color. Other parameters include the sound that should be played through the speaker in the dome light and at other stations. This "database" is stored in the primary console. The parameters specific to the dome light are also stored in the I/O Board. When the I/O Board determines that there is a call originating in the room that it is responsible for, it uses those stored parameters to determine how to illuminate the light guides. It does so by pulling the parameters from the list based on the call type.

Figure 15:
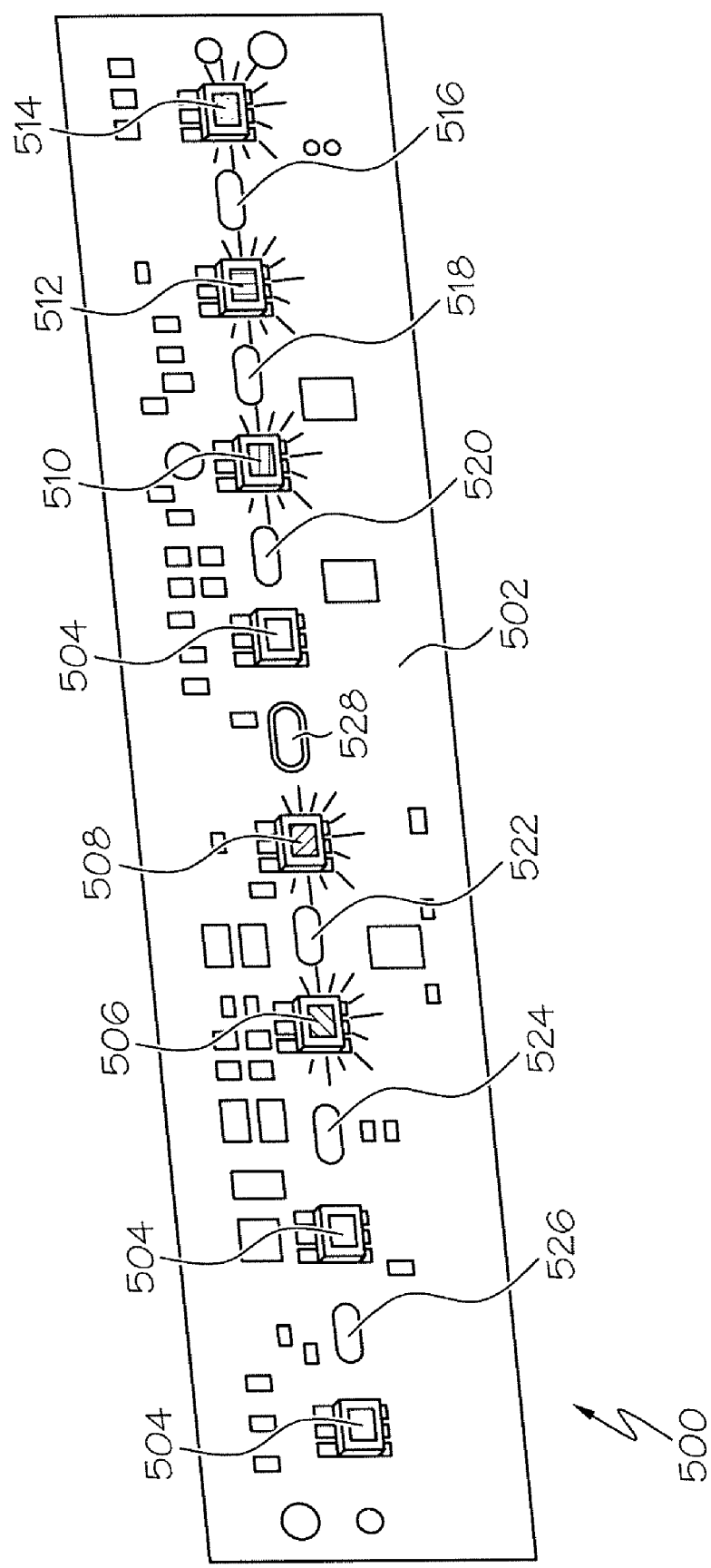
FIG. 15 is a top perspective view of a printed circuit board for an indicator assembly of the type shown in FIG. 8, showing electrical circuitry and a plurality of light sources.

FIG. 15 illustrates an embodiment of a circuit board 500 suitable for use in an indicator assembly as described above. Circuit board 500 includes a substrate 502, a plurality of surface mounted tri-color LEDs mounted thereto so that light is projected outwardly from the LEDS away from the board 500 and generally perpendicularly to the board 500. LEDs 504 are shown as being unlit, while LEDs 506, 508, 510, 512, 514 are shown as being lit, with each of them being lit in a different color. Different colors may be achieved by varying the combination of colors activated at the LED or their intensity. LEDs are arranged in a longitudinal line down the central portion of the board 500. Alternating in line with the LEDs are holes 516, 518, 520, 528, 522, 524, 526. These holes are configured to receive the light guide feet or pins to mount the light guides to the board 500 so that an LED is positioned underneath the central portion of the light guide as described above.

Figure 16:
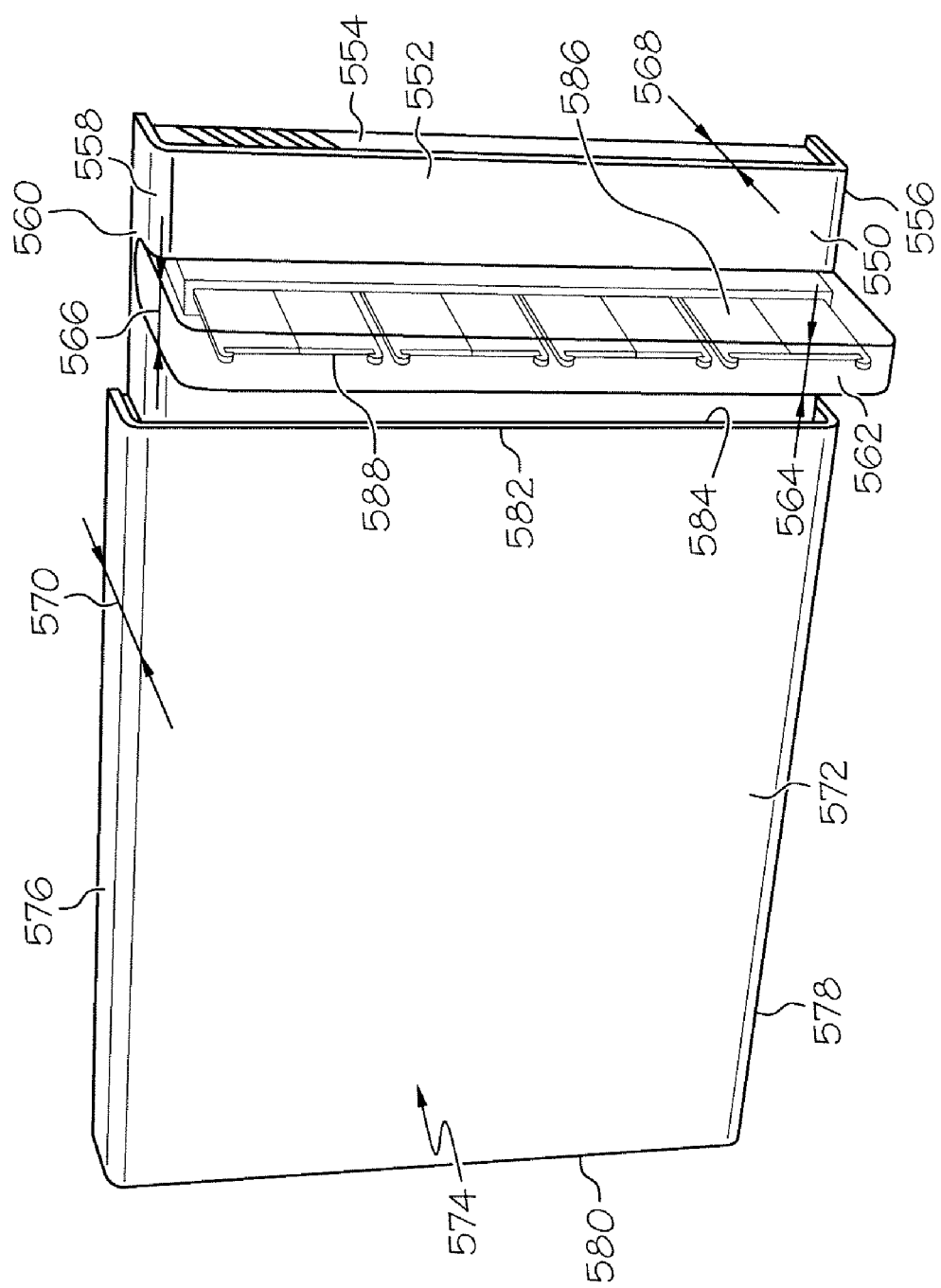
FIG. 16 is a perspective view of an indicator assembly nested with an electronic assembly, such as an input-output board, of a patient-nurse communication system and mounted to a wall in a vertical orientation.

For architectural efficiencies and/or other reasons, an electronic assembly may be mounted adjacent to an indicator assembly in a facility as shown in FIG. 16. In the embodiment of FIG. 16, I/O board 574 is mounted on a wall in an adjacent to an indicator assembly 550, which is mounted in a vertical orientation as shown. Indicator assembly 550 has a top face 552, a rear mounting plate (not visible), a top end 558, a first side 554, a bottom end 556 and a second side (not visible). The second side is adjacent to and may abut a portion of the first end 582 of the I/O board 574 underneath lip 584. As such, a portion of the I/O board housing slides over a portion of the indicator housing 552.

With regard to indicator assembly 550, FIG. 16 also shows light guides 586 positioned within an interior region defined by a cover 562, and cover 562 has a top thickness 564, which is substantially the same as side thickness 566. Each light guide 586 has a substantially planar top end 588 as shown. In the illustrated embodiment, the top ends 588 of the light guides have a thickness of about 3 millimeters while the bottom ends, located within the slot 560, have a thickness that is greater than the top thickness.

I/O board 574 has a housing including first end 582, second end 580, top side 576 and bottom side 578. Within the interior region of the housing, computer components and circuitry are provided. I/O board 574 has a thickness or depth 570 that is greater than the thickness or depth 568 of the indicator assembly housing, thus enabling a portion of top cover 572 to fit over a portion of the indicator housing.

Figure 17:
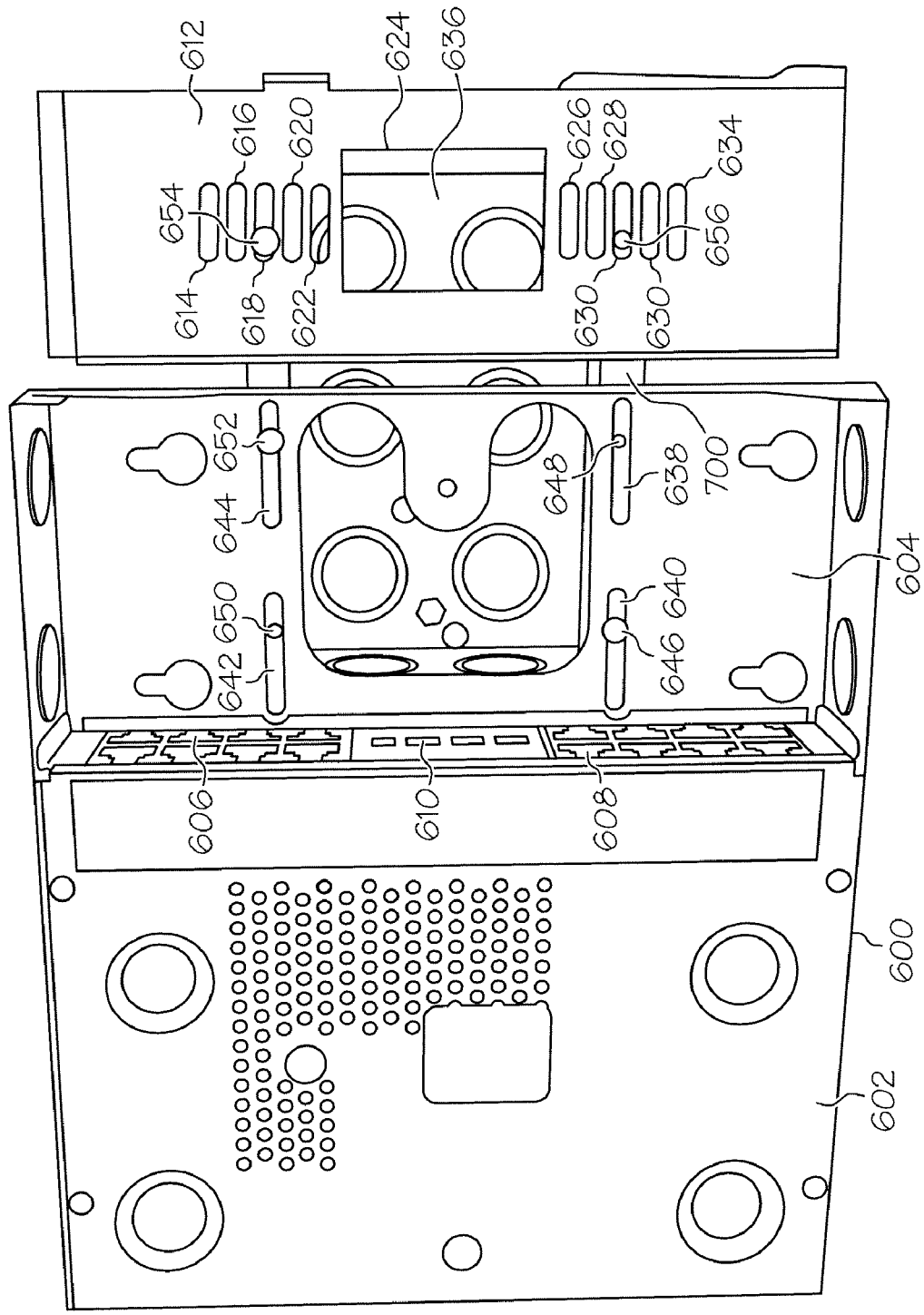
FIG. 17 is a perspective view of the electronic assembly of FIG. 16, with the cover removed and showing a mounting portion mounted to a mounting apparatus in a vertical orientation, and a mounting plate for the indicator assembly also mounted to the mounting apparatus adjacent the electronic assembly.

FIG. 17 shows the I/O board 574 with the top cover 572 removed. I/O board 580 has an interior housing 600, which includes a main portion 602 and a mounting portion 604. I/O board components and circuitry are located within the main portion 602. A plurality of data, communication, and power connector ports 606, 608, 610 are provided. RJ45 cabling connects to indicator assembly at port 342, is routed through aperture 314 behind mounting plates 604, 308 and connected to I/O board 574 at one of these ports.

Figure 18:
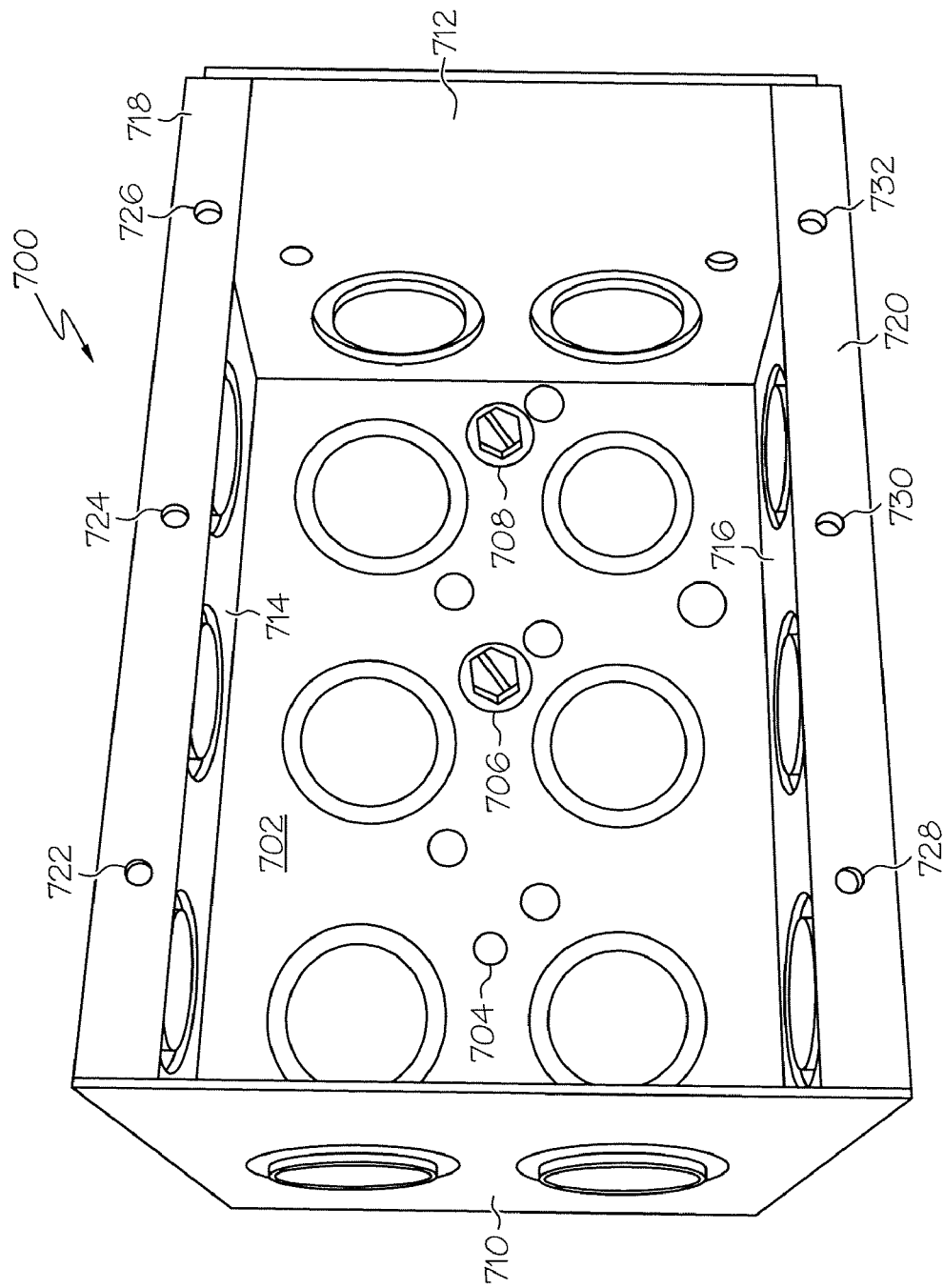
FIG. 18 is a perspective view of the mounting apparatus of FIG. 17.

I/O board mounting plate 604 and indicator assembly mounting plate 308 are mounted to a backbox 700, which in turn is mounted to a wall of a facility by screws 704, 706, 708 extending through holes in back face 702 of box 700. Mounting plate 604 includes mounting regions 638, 630, 642, 644, which are holes or apertures through which pins or screws 646, 648, 650, 652 are inserted and connected to mounting portions 722, 724, 728, 730 of backbox 700 as shown in FIG. 18.

Mounting plate 308 of the indicator assembly includes mounting regions 310, 312 as described above. Each mounting portion 310, 312 includes a plurality of holes or apertures 614, 616, 618, 620, 622, 626, 628, 630, 632, 634, which are each configured to receive a mounting pin or screw, e.g. screws 654, 656. Screws 654, 656 connect to mounting holes 726, 732 of box 700 to mount the indicator assembly thereto. Box 700 has a top 714, a bottom 716 and sides 710, 712 extending outwardly from back face 702. Box 700 also has mounting strips 718, 720 extending along top 714 and bottom 716 and substantially perpendicularly therefrom. Mounting holds 722, 724, 726, 728, 730, 732 are provided in the mounting strips.

The Appendices filed with U.S. Provisional Patent Application Ser. No. 61/066,883 contain additional details relating to features of the described indicator assembly and other subject matter disclosed herein.

The present disclosure describes patentable subject matter with reference to certain illustrative embodiments. The drawings are provided to facilitate understanding of the disclosure, and may depict a limited number of elements for ease of explanation. Except as may be otherwise noted in this disclosure, no limits on the scope of patentable subject matter are intended to be implied by the drawings. Variations, alternatives, and modifications to the illustrated embodiments may be included in the scope of protection available for the patentable subject matter.

The invention claimed is:

1. An indicator apparatus for a patient-nurse communication system, comprising:
   a base mountable to a wall or a ceiling,
   at least one visual indicator supported by the base, the at least one visual indicator being configured to display one or more of a plurality of colors,
   electrical circuitry operably coupled to the at least one visual indicator and configured to receive electrical signals indicative of at least one color to be displayed by the at least one visual indicator in response to a call from a call-originating device of the patient-nurse communication system, wherein the at least one color to be displayed is variable depending on a call type, and
   a speaker, wherein the electrical circuitry is configured to receive an electrical signal from the patient-nurse communication system to play a sound file through the speaker in response to the call from the call-originating device of the patient-nurse communication system, and the sound file to be played is variable depending on the call type.

2. The indicator apparatus of claim 1, comprising a plurality of visual indicators operably coupled to the electrical circuitry to display at least one color in response to calls from the call-originating device of the patient-nurse communication system, wherein the electrical circuitry is configured to send a first electrical signal indicative of at least one color to a first visual indicator of the plurality of visual indicators in response to a first call and send a second electrical signal indicative of at least one color to a second visual indicator of the plurality of visual indicators in response to a second call.

3. The indicator apparatus of claim 1, wherein each visual indicator has a length, a width, and a thickness, and the thickness of the visual indicator is less than the length and the thickness of the visual indicator is less than the width.

4. The indicator apparatus of claim 1, comprising a cover defining an interior region, wherein the at least one visual indicator is positioned in the interior region, the cover has first and second faces that are spaced by a thickness, and the first and second faces are substantially parallel.

5. The indicator apparatus of claim 1, wherein the at least one color to be displayed is variable depending on criteria relating to at least one of the call-originating device, call type, call priority, and patient location.

6. A patient-nurse communication system, comprising:
an indicator apparatus comprising a base mountable to a wall or a ceiling, a multi-color light source supported by the base, and electrical circuitry operably coupled to the light source and configured to receive electrical signals from the patient-nurse communication system indicative of at least one color to be displayed by the light source,
a memory comprising at least one parameter relating to a call from a call-originating device of the patient-nurse communication system, and
computer circuitry configured to access the memory, read the at least one parameter, identify at least one color to be illuminated by the light source based on the at least one parameter, and send an electrical signal to the light source to illuminate the at least one selected color in response to the call.

7. The patient-nurse communication system of claim 6, wherein the at least one parameter associates a call type of the call from the call-originating device with a color.

8. The patient-nurse communication system of claim 6, wherein the indicator assembly comprises a speaker, and the computer circuitry is configured to execute computer program logic to select a sound file in response to the call from the call-originating device of the patient-nurse communication system and send an electrical signal to the indicator assembly to play the sound file through the speaker in response to the call.

9. The patient-nurse communication system of claim 8, comprising a memory, wherein the sound file is one of a plurality of sound files stored in the memory.

10. The patient-nurse communication system of claim 6, wherein the computer circuitry is configured to receive data indicative of changes to the at least one parameter from a network and store the parameter changes in the memory.

11. The patient-nurse communication system of claim 6, comprising a visual indicator illuminatable by the light source, wherein the visual indicator has a length, a width, and a thickness, and the thickness of the visual indicator is less than the length and the thickness of the visual indicator is less than the width.

12. The patient-nurse communication system of claim 11, wherein the visual indicator has a first face and a second face spaced from the first face by the thickness to define an interior region of the visual indicator, and the interior region of the visual indicator comprises plastic.

13. The patient-nurse communication system of claim 6, comprising a cover defining an interior region, wherein a visual indicator is positioned in the interior region, the visual indicator is illuminatable by the light source, the cover has first and second faces that are spaced by a thickness, and the first and second faces are substantially parallel.

14. The patient-nurse communication system of claim 13, wherein the visual indicator comprises a plurality of light guides positioned in the interior region and aligned in a plane that is substantially parallel to the first and second faces.

15. An indicator apparatus for a patient-nurse communication system, comprising:
an indicator housing,
a cover coupled to the indicator housing and defining an interior region,
a plurality of visual indicators extending from the indicator housing and located in the interior region of the cover, the visual indicators being configured to selectively illuminate in response to signals received from a call-originating device of the patient-nurse communication system,
a mounting plate coupled to the indicator housing, the mounting plate including a first mounting portion and a second mounting portion spaced from the first mounting portion, each mounting portion having a plurality of vertically aligned and laterally elongated mounting ports, and
an elongated slot defined by the indicator housing, wherein the slot is configured to receive a visual indicator in either a first orientation or a second orientation substantially perpendicular to the first orientation.

16. The indicator apparatus of claim 15, wherein the indicator housing has a first thickness, further comprising a second housing spaced from the indicator housing and defining a second interior region, electronic circuitry located in the second interior region, the electronic circuitry being operably coupled to the visual indicators, the second housing having a second thickness, wherein the first thickness is less than the second thickness.

17. The indicator assembly of claim 16, wherein the indicator housing is mountable to the first mounting portion and the second housing is mountable to the second mounting portion.

18. An indicator apparatus for a patient-nurse communication system, comprising:
a base mountable to a wall or a ceiling,
at least one visual indicator supported by the base, the at least one visual indicator being configured to display one or more of a plurality of colors, and
electrical circuitry operably coupled to the at least one visual indicator and configured to receive electrical signals indicative of at least one color to be displayed by the at least one visual indicator in response to a call from a call-originating device of the patient-nurse communication system, wherein each of the at least one visual indicators comprises at least one face and opposing edges adjacent the at least one face, wherein the at least one face is configured to display the at least one color across the at least one face and each edge is configured to prevent the displayed color from bleeding over to an adjacent visual indicator; and
a speaker, wherein the electrical circuitry is configured to receive an electrical signal from the patient-nurse communication system to play a sound file through the speaker in response to the call from the call-originating device of the patient-nurse communication system, and the sound file to be played is variable depending on a call type.

* * * * *